(12) United States Patent
Baltruschat et al.

(10) Patent No.: US 6,683,027 B2
(45) Date of Patent: Jan. 27, 2004

(54) HERBICIDAL MIXTURES

(75) Inventors: Helmut Siegfried Baltruschat, Schweppenhausen (DE); Astrid Brandt, Mainz (DE)

(73) Assignee: BASF Aktienegesellschaft, Ludwigshafen (DE)

( * ) Notice: Subject to any disclaimer, the term of this patent is extended or adjusted under 35 U.S.C. 154(b) by 133 days.

(21) Appl. No.: 09/938,370

(22) Filed: Aug. 24, 2001

(65) Prior Publication Data

US 2002/0055435 A1 May 9, 2002

Related U.S. Application Data

(60) Provisional application No. 60/228,317, filed on Aug. 25, 2000.

(51) Int. Cl.⁷ ..................... A01N 43/54; A01N 25/32; A01N 39/04; A01N 47/30; A01N 61/00
(52) U.S. Cl. ..................... 504/128; 504/132; 504/134; 504/136; 504/242
(58) Field of Search ................. 504/136, 128, 504/132, 134, 242

(56) References Cited

U.S. PATENT DOCUMENTS

| | | | |
|---|---|---|---|
| 4,493,726 A | 1/1985 | Burdeska et al. | 71/87 |
| 5,163,995 A | 11/1992 | Van Heertum et al. | 71/92 |
| 2002/0039968 A1 * | 4/2002 | Aven et al | 504/128 |
| 2002/0049141 A1 * | 4/2002 | Baltruschat et al. | 504/236 |

FOREIGN PATENT DOCUMENTS

| | | |
|---|---|---|
| CA | 2334955 | 12/1999 |
| EP | 0 055 693 | 7/1982 |
| EP | 0 723 960 | 7/1996 |
| WO | WO 99/24427 | 5/1999 |
| WO | WO 99/65314 | 12/1999 |
| WO | WO 01/90080 | 11/2001 |
| WO | WO 01/97613 | 12/2001 |

OTHER PUBLICATIONS

Klaus Grossmann, Helmut Schiffer, *Pesticide Science*, 55:687–695 (1999).

* cited by examiner

*Primary Examiner*—S. Mark Clardy
(74) *Attorney, Agent, or Firm*—Keil & Weinkauf

(57) ABSTRACT

The invention relates to a herbicidal composition comprising a herbicidally acceptable carrier and/or surface active agent and, as active ingredient, a synergistically effective amount of (1) at least one compound of formula I:

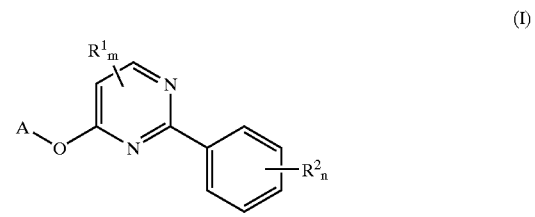

in which $R^1$, $R^2$, A, m and n are as defined in claim 1; and (2) at least one additional herbicidal compound, which is active against broad-leaved weeds and/or annual grasses; and/or (3) at least one additional safening compound;

which provides a synergistic effect against a broad spectrum of weed species, e.g., in cereal crops and/or reduces crop injuries.

The invention also provides a respective method for controlling weeds and/or reducing crop injuries.

23 Claims, No Drawings

HERBICIDAL MIXTURES

This application claims priority from copending provisional application serial No. 60/228,317 filed on Aug. 25, 2000.

BACKGROUND OF THE INVENTION

The present invention relates to an improvement in the efficacy of herbicidal 2-phenyl-4-(hetero-)aryloxypyrimidines by combination with a selected second herbicidal compound and/or a safener.

The herbicidal 2-phenyl-4-(hetero-)aryloxypyrimidines to be used according to the present invention are a group of compounds, disclosed for example by the European Patent Application EP 0 723 960, which display excellent herbicidal performance, in particular against broad-leaved weeds in cereal crops. However, the 2-phenyl-4-(hetero-)aryloxypyrimidines, when used as the sole active ingredient, do not always achieve effective control of the full spectrum of weed species encountered in commercial agronomic applications, in conjunction with reliable selectivity for the crop species. Such gaps in the spectrum of control can be overcome by co-treatment with another herbicide known to be effective against the relevant weed species and/or with a safener to reduce crop injury.

SUMMARY OF THE INVENTION

The present invention relates to a herbicidal composition comprising, as active ingredient, a synergistically effective amount of (1) at least one 2-phenyl-4-(hetero-)aryloxypyrimidines of formula I

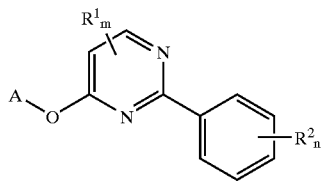

(I)

wherein
A represents an optionally substituted phenyl group or an optionally substituted 5- or 6-membered nitrogen-containing heteroaromatic group or a difluorobenzodioxolyl group;
m represents an integer from 0 to 2;
n represents an integer from 0 to 5;
$R^1$ (or each $R^1$) independently represents a halogen atom, an optionally substituted alkyl, alkenyl, alkinyl, alkoxy, alkoxyalkyl, dialkoxyalkyl, alkoxyalkoxy, alkylthio, amino, alkylamino, dialkylamino, alkoxyamino or formamidino group;
$R^2$ (or each $R^2$) independently represents a halogen atom, an optionally substituted alkyl, alkenyl, alkinyl, haloalkyl, haloalkoxy, alkoxy, alkoxyalkyl, alkoxyalkoxy, alkylthio, haloalkylthio group or a nitro, cyano, $SF_5$ or a alkylsulphonyl or alkylsulfinyl group; or its environmentally compatible salts;
(2) at least one additional herbicidal compound, which is active against broad-leaved weeds and/or annual grasses;
and/or
(3) at least one additional safening compound.

The present invention also includes a method for controlling undesirable plant species comprising application of at least one compound of group (1) and at least one compound of group (2), and/or at least one compound of group (3), as defined above. In the method of this invention, these compounds may be applied separately or together, in herbicidally effective and/or safening amounts.

DETAILED DESCRIPTION OF THE PREFERRED EMBODIMENTS

Surprisingly, it has now been found, that the combined herbicidal activity of compounds from the above mentioned 2-phenyl-4-(hetero-)aryloxypyrimidines with various compounds of group (2) against many broad-leaved weeds and annual grasses is much greater than expected when applied pre- or post-emergence and that this activity cannot be ascribed to an additive effect, but to a remarkable degree of synergism on many broad-leaved weed species and annual grasses, for example on grass weeds such as *Alopecurus myosuroides, Apera spica-venti, Lolium perenne, Setaria viridis*, and broadleaf weeds such as *Galium aparine, Lamium purpureum, Matricaria inodora, Papaver rhoeas, Stellaria media* and *Veronica persica*. (i.e. the combinations according to the invention show a much higher level of activity than predicted from that of the individual compounds) which enables also a greater selectivity for the crop species.

Also it has been found now that injuries on crop plants caused by a compound of group (1) or by a mixture of a compound of group (1) and a compound of group (2) may be reduced by additionally applying a compound of group (3).

A mixture of herbicides shows synergistic effect if the herbicidal activity of the mixture is larger than the sum of activities of the separately applied compounds. The expected herbicidal activity for a given mixture of two herbicides can be calculated as follows (See Colby, S. R., "Calculating synergistic and antagonistic response of herbicide combinations", Weeds 15, pp 20–22 (1967):

$$WE = X + \frac{Y \times (100 - X)}{100}$$

wherein
X is the percentage of growth inhibition upon treatment with a herbicide 1 at a dose of p kg/ha compared with an untreated control (X=0%)
Y is the percentage of growth inhibition treatment with a herbicide 2 at a dose of q kg/ha compared with an untreated control
WE is the herbicidal effect to be expected upon treatment (% of growth inhibition compared with untreated control) with a combination of herbicide 1 and 2 at a dose of p+q g/ha, respectively.
If the actual weed control (W) exceeds the expected (calculated) weed control (WE), the mixture displays a synergistic effect.

The compounds of group (1), (2) and (3) can exist, or be used, in the form of the pure enantiomers and also as racemates or diastereomer mixtures.

They may also exist in the form of their environmentally compatible salts, esters, thioesters and amides.

Suitable salts, esters, thioesters and amides are, in general, those ones which do not adversely affect the herbicidal action of the active ingredients.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, it being possible in this case, if desired, for one to four hydrogen atoms to be replaced by $C_1$–$C_4$-alkyl, hydroxy-$C_1$–$C_4$-alkyl, $C_1$–$C_4$-alkoxy-$C_1$–$C_4$-alkyl, hydroxy-$C_1$–$C_4$-alkoxy-$C_1$–$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-yl ammonium, di(2-hydroxyeth-1-yl)ammonium, trimethylbenzylammonium, furthermore phosphonium ions, sulfonium ions, preferably tri($C_1$–$C_4$-alkyl)sulfonium and sulfoxonium ions, preferably, tri($C_1$–$C_4$-alkyl)sulfoxonium.

Anions of suitable acid addition salts are mainly chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$–$C_4$-alkanoic acids, preferably formate, acetate, propionate and butyrate.

Suitable esters are alkyl-, alkoxyalkyl-, allyl- and propargyl-esters, especially $C_{1-10}$-alkyl esters for example methyl-, ethyl-, propyl-, isopropyl-, butyl-, isobutyl-, pentyl-, mexyl-(1-methylhexyl) or isooctyl(2-ethylhexyl) ester, $C_{1-4}$alkoxyethylester for example methoxyethyl-, ethoxyethyl- or butoxyethylester, allyl esters and propargyl esters.

Suitable thioesters are alkylthioesters, especially $C_{1-10}$-alkylthio esters for example ethylthio ester.

Suitable amides are alkyl amides, especially methyl amide and dimethylamide, and aryl amides like phenyl amide or 2-chloro-phenyl amide.

The organic moieties mentioned for the substituents $R^1$, $R^2$ and $R^a$ to $R^f$ or as radicals on phenyl or heteroaromatic rings represent collective terms for individual enumerations of the individual group members. All hydrocarbon chains, ie. all alkyl, haloalkyl, alkoxy, haloalkoxy, alkylthio, alkylsulfinyl, alkylsulfonyl and alkoxycarbonyl moieties can be straight chain or branched. Unless otherwise specified, halogenated substituents preferably have attached to them one to five identical or different halogen atoms. Halogen means in each case fluorine, chlorine, bromine or iodine.

Examples for other meanings are:

$C_{1-2}$ alkyl: methyl or ethyl;

$C_{1-4}$ alkyl: $C_{1-2}$ alkyl as mentioned above, and also n-propyl, 1-methylethyl, butyl, 1-methylpropyl, 2-methylpropyl or 1,1-methylethyl;

$C_{1-6}$ alkyl: $C_{1-4}$ alkyl as mentioned above, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylbutyl, 1-ethyl-1-methylpropyl or 1-ethyl-2-methylpropyl;

$C_{1-4}$ haloalkyl: $C_{1-4}$ alkyl as mentioned above which are partially or fully substituted by fluorine, chlorine, bromine and/or iodine, eg. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromoethyl)-2-bromoethyl, 4-fluorobutyl, 4-chlorobutyl, 4-bromobutyl or nonafluorobutyl;

$C_{1-6}$-haloalkyl: $C_{1-4}$ haloalkyl as mentioned above, and also 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_{1-4}$ alkoxy and the alkoxy part of $C_{1-4}$ alkoxycarbonyl: methoxy, ethoxy, propyoxy, 1-methylethoxy, butoxy, 1-methylpropoxy, 2-methylpropoxy or 1,1-methylethoxy;

$C_{1-6}$ alkoxy: $C_{1-4}$ alkoxy as mentioned above, and also pentoxy, 1-methylbutoxy, 2-methylbutoxy, 3-methylbuoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylbutoxy, 1-ethyl-1-methylpropoxy or 1-ethyl-2-methylpropoxy;

$C_{1-4}$ haloalkoxy: $C_{1-4}$ alkoxy as mentioned above which are partially or fully substituted by fluorine, chlorine, bromine and/or iodine, eg. dichloromethoxy, trichloromethoxy, fluoromethoxy, difluoromethoxy, trifluoromethoxy, bromodifluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromoethyl)-2-bromoethoxy, 4-fluorobutoxy, 4-chlorobutoxy, 4-bromobutoxy or nonafluorobutoxy;

$C_{1-6}$ haloalkoxy: $C_{1-4}$ haloalkoxy as mentioned above, and also 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

$C_{1-6}$ alkylsulfinyl ($C_{1-6}$alkyl-(S=O)—): methylsulfinyl, ethylsulfinyl, n-propylsulfinyl, 1-methylethylsulfinyl, butylsulfinyl, 1-methylpropylsulfinyl, 2-methylpropylsulfinyl, 1,1-methylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, hexylsulfinyl, 1,1-dimethylpropylsulfinyl, 1,2-dimethylpropylsulfinyl, 1-methylethylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylbutylsulfinyl, 1-ethyl-1-methylpropylsulfinyl or 1-ethyl-2-methylpropylsulfinyl;

$C_{1-6}$ alkylsulfonyl ($C_{1-6}$alkyl-(S=O)$_2$—): methylsulfonyl, ethylsulfonyl, n-propylsulfonyl, 1-methylethylsulfonyl, butylsulfonyl, 1-methylpropylsulfonyl, 2-methylpropylsulfonyl, 1,1-methylethylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylbutylsulfonyl, 1-ethyl-1-methylpropylsulfonyl or 1-ethyl-2-methylpropylsulfonyl.

Preferred embodiments of the present invention include those wherein A is a 5- or 6-membered heteroaryl group comprises optionally substituted 5- or 6-membered heterocycles containing one or more nitrogen and/or oxygen and/or sulfur atoms, 1 to 3 nitrogen atoms being preferred. Examples of such groups are pyrazolyl, imidazolyl, triazolyl, tetrazolyl, pyridyl, pyrazinyl, pyrimidyl, pyridazinyl, isoxazolyl, isothiazolyl and triazinyl groups.

Generally, if any of the above mentioned moieties comprises an alkyl, alkenyl or alkynyl group, such groups, unless otherwise specified, may be linear or branched and may contain up to 12, preferably up to 4, carbon atoms. Examples of such groups are methyl, ethyl, propyl, vinyl, allyl, isopropyl, butyl, isobutyl and tertiary-butyl groups. The alkyl portion of a haloalkyl, haloalkoxy, alkylthio, haloalkylthio, alkoxy, alkylamino, dialkylamino, alkoxyamino, alkylsulfinyl or alkylsulfonyl group suitably has from 1 to 4 carbon atoms, preferably 1 or 2 carbon atoms. The number of carbon atoms in the alkoxyalkyl, alkoxyalkoxy or dialkoxyalkyl groups is up to 6, preferably up to 4, e.g. methoxymethyl, methoxymethoxy, methoxyethyl, ethoxymethyl, ethoxyethoxy, dimethoxymethyl.

"Halogen" means a fluorine, chlorine, bromine or iodine atom, preferably fluorine, chlorine or bromine. Haloalkyl, haloalkylthio and haloalkoxy are preferably mono-, di- or trifluoroalkyl, -alkylthio and -alkoxy, especially trifluoromethyl, difluoromethoxy, trifluoromethylthio and trifluoromethoxy.

When any groups are designated as being optionally substituted, the substituent groups which are optionally present may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds. There may be one or more of the same or different substituents present in each part of the molecules.

In relation to moieties defined above as comprising an optionally substituted aryl or heteroaryl group, optional substituents include halogen, especially fluorine, chlorine and bromine atoms, and nitro, cyano, amino, hydroxyl, $C_{1-4}$-alkyl, $C_{1-4}$-alkoxy, $C_{1-4}$alkylthio, $C_{1-4}$-haloalkoxy, $C_{1-4}$-haloalkylthio. 1 to 5 substituents may suitably be employed, 1 to 2 substituents being preferred.

In relation to moieties defined above as comprising an optionally substituted alkyl group, including alkyl parts of haloalkyl, alkoxy, alkoxyalkyl, dialkoxyalkyl, alkoxyalkoxy, alkylthio, haloalkoxy, alkylamino, dialkylamino, alkoxyamino, alkylthio, haloalkylthio, alkylsulfinyl and alkylsulfonyl groups, specific examples of such substituents include phenyl, halogen atoms, nitro, cyano, hydroxyl, $C_{1-4}$-alkoxy, $C_{1-4}$-haloalkoxy and $C_{1-4}$-alkoxycarbonyl groups.

In relation to moieties defined above as comprising an optionally substituted alkenyl or alkynyl group specific examples of such substituents include phenyl, halogen atoms, nitro, cyano, $C_{1-4}$-alkoxy, $C_{1-4}$-haloalkoxy and $C_{1-4}$-alkoxycarbonyl groups.

The index m preferably means 0 or 1, n is preferably 1 or 2.

Preferred compounds for use as 2-phenyl-4-(hetero-)aryloxypyrimidine according to the invention are the compounds of formula I, wherein A represents a phenyl group being substituted by 1 to 5 radicals of the group consisting of halogen, especially fluorine, chlorine and bromine atoms, nitro, cyano, $C_{1-4}$-alkyl, $C_{1-4}$-alkoxy, $C_{1-4}$-haloalkyl, $C_{1-4}$-haloalkoxy, $C_{1-4}$-alkylthio, $C_{1-4}$-haloalkylthio;

especially a phenyl group being substituted by 1 or 2 radicals of the group consisting of halogen, especially fluorine, chlorine and bromine atoms, $C_{1-4}$-alkyl, $C_{1-4}$-alkoxy, $C_{1-4}$-haloalkyl and $C_{1-4}$-haloalkoxy; or represents a 5- or 6-membered heteroaryl group containing one or two nitrogen atoms being substituted by 1 to 5 radicals of the group consisting of halogen, especially fluorine, chlorine and bromine atoms, nitro, cyano, $C_{1-4}$-alkyl, $C_{1-4}$-alkoxy, $C_{1-4}$-haloalkyl, $C_{1-4}$-haloalkoxy, $C_{1-4}$-alkylthio, $C_{1-4}$-haloalkylthio; especially a pyrazolyl or a pyridyl group being substituted by 1 or 2 radicals of the group consisting of halogen, especially fluorine, chlorine and bromine atoms, $C_{1-4}$-alkyl, $C_{1-4}$-alkoxy, $C_{1-4}$-haloalkyl and $C_{1-4}$-haloalkoxy;

$R^2$ represents a halogen atom, especially fluorine, chlorine or bromine, $C_{1-4}$-alkyl, $C_{1-4}$-alkoxy, $C_{1-4}$-haloalkyl and $C_{1-4}$-haloalkoxy; especially chlorine, flourine, methyl, methoxy, trifluoromethyl, difluoromethoxy or trifluoromethoxy, m is 0;

n is 0, 1 or 2.

Especially preferred are compounds of formula I, wherein

A represents a phenyl group being substituted by one chlorine or fluorine atom, or one methyl, trifluoromethyl, trifluoromethoxy or difluoromethoxy group;

m is 0;

n is 1 or 2.

In particular 4-(3-trifluoromethylphenoxy)-2-(4-trifluoromethylphenyl)-pyrimidine coded Compound A.

The additional compounds of group (2) having herbicidal activities against broad-leaved weeds and/or annual grasses are selected from a) lipid biosnthesis inhibitors;
b) acetolactate synthase inhibitors (ALS);
c) photosynthesis inhibitors;
d) protoporphyrinogen-IX-oxidase inhibitors;
e) bleacher herbicides;
f) enolpyruvylshikimate 3-phosphate synthase inhibitors (EPSP);
g) glutamine synthetase inhibitors;
h) dihydropteroate synthase inhibitors (DHP);
i) mitosis inhibitors;
j) cell division inhibitors;
k) cellulose biosynthesis inhibitors,
l) uncoupling herbicides;

m) auxin herbicides;
n) auxin transport inhibitors; or
o) various other herbicides;

Examples of herbicides of group (2) which can be used in combination with the compounds of formula I according to the present invention are, inter alia:

a) lipid biosnthesis inhibitors like chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, propaquizafop, quizalofop, quizalofop-P, trifop, alloxydim, butroxydim, clethodim, cloproxydim, cycloxydim, profoxydim, sethoxydim, tepraloxydim, tralkoxydim, butylate, cycloate, di-allate, dimepiperate, EPTC, esprocarb, ethiolate, isopolinate, methiobencarb, molinate, orbencarb, pebulate, prosulfocarb, sulfallate, thiobencarb, tiocarbazil, tri-allate, vernolate, bensulide, benfuserate or ethofumesate;

b) acetolactate synthase inhibitors like
   sulfonyl urea type herbicides for example amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, propoxycarbazon or flucarbazon;
   sulfonamide type herbicides for example chloransulam, diclosulam, florasulam, flumetsulam, metosulam or penoxsulam;
   imidazolinone type herbicides for example imazamethabenz, imazamox, imazapic, imazapyr, imazaquin or imazethapyr;
   pyrimidyl ethers for example bispyribac, pyribenzoxim, pyriftalid, pyrithiobac or pyriminobac;

c) photosynthesis inhibitors like
   photosynthetic electron transport inhibitors
      such as triazine type herbicides for example ametryn, atraton, atrazine, aziprotryne, chlorazine,cyanatryn, cyanazine, cyprazine, desmetryne, dimethamethryn, dipropetryn, egliazine, ipazine, mesoprazine, methometon, methoprotryn, procyazine, proglinazine, prometon, prometryn, propazine, sebuthylazine, secbumeton, simazine, simeton, simetryn, terbumeton, terbutylazine, terbutryn or trietazine; or
      such as urea type herbicides for example anisuron, benzthiazuron, buthiuron, buturon, chlorbromuron, chloreturon, chlorotoluron, chloroxuron, difenoxuron, dimefuron, diuron, ethidimuron, fenuron, fluometuron, fluothiuron, isoproturon, isouron, linuron, methabenzthiazuron, methiuron, metobenzuron, metobromuron, metoxuron, monoisouron, monolinuron, monuron, neburon, parafluron, phenobenzuron, siduron, tebuthiuron, tetrafluron, thiadiazuron or thiazafluron;
   further photosynthesis inhibitors
      such as nitrile type herbicides for example bromobonil, bromoxynil, chloroxynil, iodobonil or ioxynil;
      such as triazinone type herbicides for example ametridione, amibuzin, hexazinone, isomethiozin, metamitron or metribuzin;
      such as uracil type herbicides for example bromacil, isocil, lenacil or terbacil;
      such as pyridazinone type herbicides for example brompyrazon, chloridazon or dimidazon;
      such as phenyl carbamate type herbicides for example desmedipham, phenisopham or phenmedipham;
      such as amide type herbicides for example propanil;
      such as benzothiadiazole type herbicides for example bentazone;
      such as phenyl pyridazine type hericides for example pyridate or pyridafol;
      such as bipyridylium type herbicides for example cyperquat, diethamquat, difenzoquat, diquat, morfamquat or paraquat;
   as well as amicarbazone, bromofenoxim, flumezin, methazole or pentanochlor;

d) protoporphyrinogen IX oxidase inhibitors like
   diphenyl ether type herbicides for example acifluorfen, bifenox, chlomethoxyfen, chlornitrofen, ethoxyfen, fluorodifen, fluoroglycofen, fluoronitrofen, fomesafen, furyloxyfen, halosafen, lactofen, nitrofen, nitrofluorfen or oxyfluorfen;
   N-phenylphthalimide type herbicides for example cinidon-ethyl, flumiclorac, flumioxazin or flumipropyn;
   thiadiazole type herbicides for example fluthiacet or thidiazimin;
   oxadiazole type herbicides for example oxadiazon or oxadiargyl;
   as well as azafenidin, carfentrazone, sulfentrazone, pentoxazone, benzfendizone, butafenacil, pyraclonil, profluazol, flufenpyr, flupropacil, nipyraclofen, etnipromid, fluazolate (JV 485) or pyraflufen;

e) bleacher herbicides like metflurazon, norflurazon, diflufenican, flufenican, picolinafen, beflubutamid, fluridone, flurochloridone, flurtamone, isoxachlortole, isoxaflutole, mesotrione, sulcotrione, benzofenap, pyrazolynate, pyrazoxyfen, benzobicyclon, amitrol, clomazone, aclonifen, ketospiradox or a 3-heterocyclyl substituted benzoyl derivative of formula II

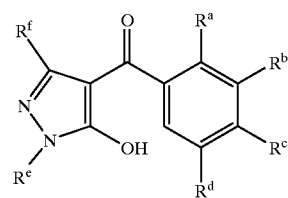

(II)

in which the variables have the following meanings:

$R^a$, $R^c$ are hydrogen, halogen, $C_{1-6}$-alkyl, $C_{1-6}$-haloalkyl, $C_{1-6}$-alkoxy, $C_{1-6}$-haloalkoxy, $C_{1-6}$-alkylthio, $C_{1-6}$-alkylsulfinyl or $C_{1-6}$-alkylsulfonyl;

$R^b$ is a heterocyclic radical selected from the group: thiazol-2-yl, thiazol-4-yl, thiazol-5-yl, isoxazol-3-yl, isoxazol-4-yl, isoxazol-5-yl, 4,5-dihydroisoxazol-3-yl, 4,5-dihydroisoxazol-4-yl and 4,5-dihydroisoxazol-5-yl, it being possible for the nine radicals mentioned to be unsubstituted or mono- or polysubstituted by halogen, $C_{1-4}$-alkyl, $C_{1-4}$-alkoxy, $C_{1-4}$-haloalkyl, $C_{1-4}$-haloalkoxy or $C_{1-4}$-alkylthio;

$R^d$ is hydrogen, halogen or $C_{1-6}$-alkyl;

$R^e$ is $C_{1-6}$-alkyl;

$R^f$ is hydrogen or $C_{1-6}$-alkyl;

f) enolpyruvylshikimate 3-phosphate synthase inhibitors (EPSP) like glyphosate;
g) glutamine synthetase inhibitors like bilanaphos or glufosinate;
h) dihydropteroate synthase inhibitors (DHP) like asulam;
i) mitosis inhibitors like
  dinitroaniline type herbicides for example benfluralin, butralin, dinitramin, ethalfluralin, fluchloralin, isopropalin, methapropalin, nitralin, oryzalin, pendimethalin, prodiamine, profluralin or trifluralin;
  phosphoramidate type herbicides for example amiprofosmethyl or butamifos;
  pyridazine type herbicides for example dithiopyr or thiazopyr;
  as well as propyzamid, tebutam, chlorthal, carbetamide, chlorbufam, chlorpropham or propham;
j) cell division inhibitors like
  chloroacetamide type herbicides for example acetochlor, alachlor, allidochlor, butachlor, butenachlor, CDEA, delachlor, diethatyl, dimethachlor, dimethenamid, dimethenamid-P, epronaz, metazachlor, metolachlor, S-metolachlor, pethoxamid, pretilachlor, propachlor, propisochlor, prynachlor, terbuchlor, thenylchlor or xylachlor;
  acetamide type herbicides for example diphenamid, napropamide or naproanilide;
  oxacetamide type herbicides for example flufenacet or mefenacet;
  as well as fentrazamide, anilophos, piperophos, cafenstrole, indanofan or tridiphane;
k) cellulose biosynthesis inhibitors like dichlobenil, chlorthiamid, isoxaben or flupoxam;
l) uncoupling herbicides like dinofenate, dinoprop, dinosam, dinoseb, dinoterb, DNOC, etinofen or medinoterb;
m) auxin herbicides like clomeprop, 2,4-D, 2,4-DB, dichlorprop, dichlorprop-P, MCPA, MCPA thioethyl, MCPB, mecoprop, mecoprop-P, 2,4,5-T, chloramben, dicamba, 2,3,6-TBA, tricamba, quinchlorac, quinmerac, clopyralid, fluroxypyr, picloram, trichlopyr or benazolin;
n) auxin transport inhibitors like naptalame or diflufenzopyr;
o) various other herbicides like
  flurene carboxylic acids for example chlorflurenol or flurenol;
  as well as benzoylprop, flamprop, flamprop-M, bromobutide, cinmethylin, cumyluron, daimuron, methyldymron, etobenzanid, fosamin, metam, pyributicarb, oxaziclomefone, dazomet, triaziflam or methylbromid;
or their environmentally compatible salts, esters, thioesters and amides.

Preferred are herbicides of group (2) such as
a) lipid biosnthesis inhibitors like clodinafop, cyhalofop, diclofop, fenoxaprop, fenoxaprop-P, fluazifop, fluazifop-P, haloxyfop, haloxyfop-P, quizalofop, quizalofop-P, alloxydim, butroxydim, clethodim, cloproxydim, cycloxydim, profoxydim, sethoxydim, tepraloxydim or tralkoxydim;
b) acetolactate synthase inhibitors like
  sulfonyl urea type herbicides for example amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysufiron, triflusulfuron, tritosulfuron, propoxycarbazon or flucarbazon;
  sulfonamide type herbicides for example chloransulam, diclosulam, florasulam, flumetsulam, metosulam or penoxsulam;
  imidazolinone type herbicides for example imazamethabenz, imazamox, imazapic, imazapyr, imazaquin or imazethapyr;
  pyrimidyl ethers for example bispyribac, pyrithiobac or pyriminobac;
c) photosynthesis inhibitors like
  photosynthetic electron transport inhibitors such as triazine type herbicides for example atrazine, cyanazine, simazine, terbutylazine, terbutryn or trietazine;
    such as urea type herbicides for example chlorbromuron, chlorotoluron, diuron, isoproturon, linuron, methabenzthiazuron or neburon;
  further photosynthesis inhibitors such as nitrile type herbicides for example bromoxynil or ioxynil;
    such as triazinone type herbicides for example hexazinone, metamitron or metribuzin;
    such as pyridazinone type herbicides for example chloridazon;
    such as amide type herbicides for example propanil;
    such as benzothiadiazole type herbicides for example bentazone;
    such as phenyl pyridazine type herbicides for example pyridate;
    such as bipyridylium type herbicides for example difenzoquat, diquat or paraquat;
    as well as amicarbazone;
d) protoporphyrinogen IX oxidase inhibitors like
  diphenyl ether type herbicides for example acifluorfen, fluoroglycofen, halosafen, lactofen or oxyfluorfen;
  N-phenylphthalimide type herbicides for example cinidon-ethyl, flumiclorac or flumioxazin;
  thiadiazole type herbicides for example fluthiacet;
  oxadiazole type herbicides for example oxadiazon or oxadiargyl;
  as well as azafenidin, carfentrazone, sulfentrazone, pentoxazone, benzfendizone, butafenacil, pyraclonil, profluazol, flufenpyr, nipyraclofen, fluazolate (JV 485) or pyraflufen;
e) bleacher herbicides like metflurazon, norflurazon, diflufenican, flufenican, picolinafen, beflubutamid, fluridone, flurochloridone, flurtamone, isoxachlortole, isoxaflutole, mesotrione, sulcotrione, benzofenap, pyrazolynate, pyrazoxyfen, benzobicyclon, clomazone, [2-chloro-3-(4,5-dihydro-3-isoxazolyl)-4-(methylsulfonyl)phenyl](5-hydroxy-1-methyl-1H-pyrazol-4-yl)methanon, [3-(4,5-dihydro-3-isoxazolyl)-2-methyl-4-(methylsulfonyl)phenyl](5-hydroxy-1-methyl-1H-pyrazol-4-yl)methanon, [2-chloro-3-(3-methyl-5-isoxazolyl)-4-(methylsulfonyl)phenyl](5-hydroxy-1-methyl-1H-pyrazol-4-yl)methanon or [3-(3-methyl-5-isoxazolyl)-2-methyl-4-(methylsulfonyl)phenyl](5-hydroxy-1-methyl-1H-pyrazol-4-yl)methanon;
f) enolpyruvylshikimate 3-phosphate synthase inhibitors (EPSP) like glyphosate;
g) glutamine synthetase inhibitors like glufosinate;
i) mitosis inhibitors like
  dinitroaniline type herbicides for example benfluralin, butralin, dinitramin, ethalfluralin, oryzalin, pendimethalin or trifluralin;

as well as propyzamid;
j) cell division inhibitors like
  chloroacetamide type herbicides for example acetochlor, alachlor, butachlor, dimethenamid, dimethenamid-P, metazachlor, metolachlor, S-metolachlor, pethoxamid, pretilachlor, propachlor, propisochlor or thenylchlor;
  oxacetamide type herbicides for example flufenacet or mefenacet;
  as well as fentrazamide, cafenstrole or indanofan;
k) cellulose biosynthesis inhibitors like dichlobenil, chlorthiamid, isoxaben or flupoxam;
m) auxin herbicides like clomeprop, 2,4-D, 2,4-DB, dichlorprop, dichlorprop-P, MCPA, MCPB, mecoprop, mecoprop-P, chloramben, dicamba, quinchlorac, quinmerac, clopyralid, fluroxypyr, picloram, trichlopyr or benazolin;
n) auxin transport inhibitors like diflufenzopyr;
o) various other herbicides like
  flurene carboxylic acids for example flurenol;
  as well as bromobutide, cinmethylin, cumyluron, daimuron, methyldymron, oxaziclomefone or triaziflam. or their environmentally compatible salts, like the sodium-, potassium-, calcium-, trimethylsulfonium-, (2-hydroxy-eth-1-yl)ammonium-, di(2-hydroxy-eth-1-yl)ammonium-, methylammonium-, trimethylammonium-, isopropylammonium-salts or nitrates, sulfates, phosphates, methylsulfates, chlorides, bromides or iodides; esters, like methyl-, ethyl-, propyl-, isopropyl-, butyl-, isobutyl-, pentyl-, mexyl-, isooctyl-, methoxyethyl-, ethoxyethyl-, butoxyethyl-, allyl- or propargyl-esters, thioesters like ethylthioesters; and amides, like methyl-, dimethyl-, phenyl- or 2-chlorphenylamides.

In another embodiment of the present invention compounds of group (2) are preferably selected from
a) lipid biosynthesis inhibitors like clodinafop or fenoxaprop; or
b) an acetolactate synthase inhibitors like
  sulfonyl urea type herbicides for example amidosulfuron, flupyrsulfuron or sulfosulfuron; or
  sulfonamide type herbicides like florasulam or metosulam; or
c) photosynthesis inhibitors like
  a photosynthetic electron transport inhibitor such as triazine-type herbicides, such as atrazine, cyanazine or simazine; or such as urea-type herbicides for example chlorotoluron, isoproturon, linuron or neburon; or
  further photosynthesis inhibitors such as nitrile type herbicides for example bromoxynil or ioxynil; or such as phenyl pyridazine type herbicides for example pyridate; or
d) protoporphyrinogen Ix oxidase inhibitors like
  N-phenylphthalimide type herbicides for example cinidon-ethyl; or
  carfentrazone or JV 485; or
i) mitosis inhibitors like
  dinitroaniline type herbicides for example pendimethalin; or
j) cell division inhibitors like
  oxacetamide type herbicides for example flufenacet; or
m) auxine herbicides like dichlorprop, MCPA, mecoprop or fluroxypyr; or
o) various other herbicides like
  fluorene carboxylic acid herbicides for example flurenol.

Examples of safeners of group (3) which can be used in combination with the compounds of formula I and optionally at least one herbicide of group (2) are, inter alia:

benoxacor, cloquintocet, cyometrinil, dichlormid, dicyclon, dietholate, fenchlorazole, fenclorim, flurazole, fluxofenim, furilazole, isoxadifen, mefenpyr, mephenate, naphthalic anhydride, oxabetrinil and R 29148.

Preferred are safeners of group (3) such as benoxacor, cloquintocet, dichlormid, fenchlorazole, fenclorim, fluxofenim, fiilazole, isoxadifen, mefenpyr and oxabetrinil.

Especially preferred are the following combinations of the compounds of group 1 and/or group 2 and/or group 3:

Compound A/clodinafop
Compound A/clodinafop/cloquintocet
Compound A/clodinafop/fenchlorazole
Compound A/clodinafop/isoxadifen
Compound A/clodinafop/mefenpyr
Compound A/cyhalofop
Compound A/cyhalofop/cloquintocet
Compound A/cyhalofop/fenchlorazole
Compound A/cyhalofop/isoxadifen
Compound A/cyhalofop/mefenpyr
Compound A/diclofop
Compound A/diclofop/cloquintocet
Compound A/diclofop/fenchlorazole
Compound A/diclofop/isoxadifen
Compound A/diclofop/mefenpyr
Compound A/fenoxaprop
Compound A/fenoxaprop/cloquintocet
Compound A/fenoxaprop/fenchlorazole
Compound A/fenoxaprop/isoxadifen
Compound A/fenoxaprop/mefenpyr
Compound A/fenoxaprop-P
Compound A/fenoxaprop-P/cloquintocet
Compound A/fenoxaprop-P/fenchlorazole
Compound A/fenoxaprop-P/isoxadifen
Compound A/fenoxaprop-P/mefenpyr
Compound A/fluazifop
Compound A/fluazifop/cloquintocet
Compound A/fluazifop/fenchlorazole
Compound A/fluazifop/isoxadifen
Compound A/fluazifop/mefenpyr
Compound A/fluazifop-P
Compound A/fluazifop-P/cloquintocet
Compound A/fluazifop-P/fenchlorazole
Compound A/fluazifop-P/isoxadifen
Compound A/fluazifop-P/mefenpyr
Compound A/haloxyfop
Compound A/haloxyfop/cloquintocet
Compound A/haloxyfop/fenchlorazole
Compound A/haloxyfop/isoxadifen
Compound A/haloxyfop/mefenpyr
Compound A/haloxyfop-P
Compound A/haloxyfop-P/cloquintocet
Compound A/haloxyfop-P/fenchlorazole
Compound A/haloxyfop-P/isoxadifen
Compound A/haloxyfop-P/mefenpyr
Compound A/quizalofop
Compound A/quizalofop/cloquintocet
Compound A/quizalofop/fenchlorazole
Compound A/quizalofop/isoxadifen
Compound A/quizalofop/mefenpyr
Compound A/quizalofop-P
Compound A/quizalofop-P/cloquintocet
Compound A/quizalofop-P/fenchlorazole
Compound A/quizalofop-P/isoxadifen
Compound A/quizalofop-P/mefenpyr
Compound A/alloxydim
Compound A/butroxydim Compound A/clethodim
Compound A/cloproxydim
Compound A/cycloxydim
Compound A/profoxydim
Compound A/sethoxydim
Compound A/tetralkoxydim
Compound A/amidosulfuron
Compound A/amidosulfuron/cloquintocet
Compound A/amidosulfuron/fenchlorazole
Compound A/amidosulfuron/isoxadifen
Compound A/amidosulfuron/mefenpyr
Compound A/amidosulfuron/furilazole
Compound A/azimsulfuron
Compound A/bensulfuron
Compound A/chlorimuron
Compound A/chlorsulfuron
Compound A/cinosulfuron
Compound A/cyclosulfamuron
Compound A/ethametsulfuron
Compound A/ethoxysulfuron
Compound A/flazasulfuron
Compound A/flupyrsulfuron
Compound A/foramsulfuron
Compound A/foramsulfuron/cloquintocet
Compound A/foramsulfuron/fenchlorazole
Compound A/foramsulfuron/isoxadifen
Compound A/foramsulfuron/mefenpyr
Compound A/foramsulfuron/furilazole
Compound A/halosulfuron
Compound A/halosulfuron/cloquintocet
Compound A/halosulfuron/fenchlorazole
Compound A/halosulfuron/isoxadifen
Compound A/halosulfuron/mefenpyr
Compound A/halosulfuron/furilazole
Compound A/imazosulfuron
Compound A/iodosulfuron
Compound A/iodosulfuron/cloquintocet
Compound A/iodosulfuron/fenchlorazole
Compound A/iodosulfuron/isoxadifen
Compound A/iodosulfuron/mefenpyr
Compound A/iodosulfuron/furilazole
Compound A/mesosulfuron
Compound A/mesosulfuron/cloquintocet
Compound A/mesosulfuron/fenchlorazole
Compound A/mesosulfuron/isoxadifen
Compound A/mesosulfuron/mefenpyr
Compound A/mesosulfuron/furilazole
Compound A/metsulfuron
Compound A/nicosulfuron
Compound A/oxasulfuron
Compound A/primisulfuron
Compound A/prosulfuron
Compound A/pyrazosulfuron
Compound A/rimsulfuron
Compound A/sulfometuron
Compound A sulfosulfuron
Compound A/thifensulfuron
Compound A/triasulfuron
Compound A/tribenuron
Compound A/trifloxysulfuron
Compound A/triflusulfuron
Compound A/tritosulfuron
Compound A/propoxycarbazon
Compound A/flucarbazon
Compound A/chloransulam
Compound A/diclosulam
Compound A/florasulam
Compound A/flumetsulam
Compound A/metosulam
Compound A/penoxsulam
Compound A/imazamethabenz
Compound A/imazamox
Compound A/imazapic
Compound A/imazapyr
Compound A/imazaquin
Compound A/imazethapyr
Compound A/bispyribac
Compound A/pyrithiobac
Compound A/pyriminobac
Compound A/pyribenzoxim
Compound A/pyriftalid
Compound A/atrazine
Compound A/cyanazine
Compound A/simazine
Compound A/terbutylazine
Compound A/terbutryn
Compound A/trietazine
Compound A/chlorbromuron
Compound A/chlorotoluron
Compound A/diuron
Compound A/isoproturon
Compound A/linuron
Compound A/methabenzthiazuron
Compound A/bromoxynil
Compound A/ioxynil
Compound A/hexazinone
Compound A/metamitron
Compound A/metribuzin
Compound A/chloridazon
Compound A/propanil
Compound A/bentazone
Compound A/pyridate
Compound A/difenzoquat
Compound A/diquat
Compound A/paraquat
Compound A/amicarbazone
Compound A/acifluorfen
Compound A/fluoroglycofen
Compound A/halosafen
Compound A/lactofen
Compound A/oxyfluorfen
Compound A/cinidon-ethyl
Compound A/flumiclorac
Compound A/flumioxazin
Compound A/fluthiacet
Compound A/oxadiazon
Compound A/oxadiargyl
Compound A/azafenidin
Compound A/carfentrazone
Compound A/sulfentrazone
Compound A/pentoxazone
Compound A/benzfendizone
Compound A/butafenacil
Compound A/pyraclonil
Compound A/profluazol
Compound A/flufenpyr
Compound A/nipyraclofen
Compound A/fluazolate (JV 485)
Compound A/pyraflufen
Compound A/norflurazon
Compound A/diflufenican
Compound A/flufenican
Compound A/picolinafen
Compound A/beflubutamid Compound A/fluridone
Compound A/flurochloridone
Compound A/flurtamone
Compound A/isoxachlortole
Compound A/isoxaflutole
Compound A/mesotrione
Compound A/sulcotrione
Compound A/benzofenap
Compound A/pyrazolynate
Compound A/pyrazoxyfen
Compound A/benzobicyclon
Compound A/clomazone
Compound A/[2-chloro-3-(4,5-dihydro-3-isoxazolyl)-4-(methylsulfonyl)phenyl](5-hydroxy-1-methyl-1H-pyrazol-4-yl)methanon
Compound A/[3-(4,5-dihydro-3-isoxazolyl)-2-methyl-4-(methylsulfonyl)phenyl](5-hydroxy-1-methyl-1H-pyrazol-4-yl)methanon
Compound A/[2-chloro-3-(3-methyl-5-isoxazolyl)-4-(methylsulfonyl)phenyl](5-hydroxy-1-methyl-1H-pyrazol-4-yl)methanon
Compound A/[3-(3-methyl-5-isoxazolyl)-2-methyl-4-(methylsulfonyl)phenyl](5-hydroxy-1-methyl-1H-pyrazol-4-yl)methanon
Compound A/glyphosate
Compound A/glufosinate
Compound A/benfluralin
Compound A/butralin
Compound A/dinitramin
Compound A/ethalfluralin
Compound A/oryzalin
Compound A/pendimethalin
Compound A/trifluralin
Compound A/propyzamid
Compound A/acetochlor
Compound A/acetochlor/dichlormid
Compound A/acetochlor/furilazole
Compound A/acetochlor/oxabetrinil
Compound A/acetochlor/fluxofenim
Compound A/acetochlor/benoxacor
Compound A/acetochlor/fenclorim
Compound A/alachlor
Compound A/butachlor
Compound A/butachlor/dichlormid
Compound A/butachlor/furilazole
Compound A/butachlor/oxabetrinil
Compound A/butachlor/fluxofenim
Compound A/butachlor/benoxacor
Compound A/butachlor/fenclorim
Compound A/dimethenamid
Compound A/dimethenamid/dichlormid
Compound A/dimethenamid/furilazole
Compound A/dimethenamid/oxabetrinil
Compound A/dimethenamid/fluxofenim
Compound A/dimethenamid/benoxacor
Compound A/dimethenamid/fenclorim
Compound A/dimethenamid-P
Compound A/dimethenamid-P/dichlormid
Compound A/dimethenamid-P/furilazole
Compound A/dimethenamid-P/oxabetrinil
Compound A/dimethenamid-P/fluxofenim
Compound A/dimethenamid-P/benoxacor
Compound A/dimethenamid-P/fenclorim
Compound A/metazachlor
Compound A/metolachlor/dichlormid
Compound A/metolachlor/furilazole
Compound A/metolachlor/oxabetinil
Compound A/metolachlor/fluxofenim
Compound A/metolachlor/benoxacor
Compound A/metolachlor/fenclorim
Compound A/S-metolachlor
Compound A/S-metolachlor/dichlormid
Compound A/S-metolachlor/furilazole
Compound A/S-metolachlor/oxabetrinil
Compound A/S-metolachlor/fluxofenim
Compound A/S-metolachlor/benoxacor
Compound A/S-metolachlor/fenclorim
Compound A/pethoxamid
Compound A/pretilachlor
Compound A/pretilachlor/dichlormid
Compound A/pretilachlor/furilazole
Compound A/pretilachlor/oxabetrinil
Compound A/pretilachlor/fluxofenim
Compound A/pretilachlor/benoxacor
Compound A/pretilachlor/fenclorim
Compound A/propachlor
Compound A/propisochlor
Compound A/thenylchlor
Compound A/flufenacet
Compound A/mefenacet
Compound A/fentrazamide
Compound A/cafenstrole
Compound A/indanofan
Compound A/dichlobenil
Compound A/chlorthiamid
Compound A/isoxaben
Compound A/flupoxam
Compound A/clomeprop
Compound A/2,4-D
Compound A/2,4-DB
Compound A/dichlorprop
Compound A/dichlorprop-P
Compound A/MCPA
Compound A/MCPB
Compound A/mecoprop
Compound A/mecoprop-P
Compound A/chloramben
Compound A/dicamba
Compound A/quinchlorac
Compound A/quinmerac
Compound A/clopyralid
Compound A/fluroxypyr
Compound A/picloram
Compound A/trichlopyr
Compound A/benazolin
Compound A/diflufenzopyr
Compound A/bromobutide
Compound A/cinmethylin
Compound A/cumyluron
Compound A/daimuron
Compound A/methyldymron
Compound A/oxaziclomefone
Compound A/triaziflam
Compound A/benoxacor
Compound A/cloquintocet
Compound A/cyometrinil
Compound A/dichlormid
Compound A/dicyclon
Compound A/dietholate
Compound A/fenchlorazole
Compound A/fenclorim
Compound A/flurazole
Compound A/fluxofenim
Compound A/furilazole Compound A/isoxadifen
Compound A/mefenpyr
Compound A/mephenate
Compound A/naphthalic anhydride
Compound A/oxabetrinil.

The pattern of persistence of the compounds of formula I is such that the combined treatment according to the present invention can be attained either by the application of a prepared mixture as defined above, or by time separated application of separate formulations.

Hence, in another preferred embodiment, the present invention provides a method for controlling the growth of weeds at a crop locus and/or reducing crop injury which comprises applying to the locus a compound of formula I as defined above and a component which is selected from those listed above as group (2) and/or a component which is selected from those listed above as group (3). Especially the application in cereals is preferred.

In another preferred embodiment, the present invention provides a method for controlling the growth of weeds at a crop locus which comprises applying to the locus a compound of formula I as defined above and a component which is selected from those listed above as group (2). Especially the application in cereals is preferred.

In another preferred embodiment, the present invention provides a method for controlling the growth of weeds at a crop locus which comprises applying to the locus a compound of formula I as defined above and a component which is selected from those listed above as group (2) and a component which is selected from those listed above as group (3). Especially the application in cereals is preferred.

In another preferred embodiment, the present invention provides a method for reducing injuries in crops which comprises applying to the locus a compound of formula I as defined above and a component which is selected from those listed above as group (3). Especially the application in cereals is preferred.

The treatment according to the invention may be used to control a broad spectrum of weed species in crops, especially in cereals e.g., in wheat, barley, rice and maize, by pre- or post-emergence treatment, including both early and late post-emergence. The combined use described above offers both foliar and residual activity.

The treatment according to the invention may be used to control a broad spectrum of weed species in crops, especially in cereals e.g., in wheat, barley, rice and maize.

The crops may be resistant to the action of herbicides as well as to insecticide attack due to breeding, including genetic engineering methods. In a embodiment of the present invention the crop may be resistant against herbicidal EPSP-inhibitors for example glyphosate, herbicidal glutamine-synthase inhibitors for example glufosinate, herbicidal protoporphyrinogen IX oxidase inhibitors for example butafenacil, or herbicidal ALS-inhibitors for example imazamethabenz, imazamox, imazapic, imazapyr, imazaquin or imazethapyr. In another embodiment of the present invention the crop may be resistant against insecticide attack due to the introduction of the gene for the Bt-toxine by genetic engineering methods.

The compositions of the present invention may be applied by pre- or post-emergence treatment, including both early and late post-emergence. The combined use described above offers both foliar and residual activity.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. It will be appreciated that application according to the method may be from pre- to post-weed emergence, and from pre-crop emergence to post-crop emergence. By the term "foliar activity" is meant herbicidal activity obtained by application to the aerial or exposed portions of the weeds which have emerged above the surface of the soil. By the term "residual activity" is meant herbicidal activity obtained some time after application to the soil whereby seedlings present at the time of application or which germinate subsequent to application are controlled. Weeds that may be controlled by the practice of the present invention include:

| | | |
|---|---|---|
| Veronica persica | Veronica hederaefolia | Stellaria media |
| Lamium purpureum | Lamium amplexicaule | Aphanes arvensis |
| Galium aparine | Alopecurus myosuroides | Matricaria inodora |
| Matricaria matricoides | Anthemis arvensis | Papaver rhoeas |
| Poa annua | Apera spica-venti | Phalaris paradoxa |
| Phalaris minor | Avena fatua | Lolium perenne |
| Bromus sterilis | Poa trivialis | Spergula arvensis |
| Cerastes holosteoides | Arenaria seryllifolia | Silene vulgaris |
| Legousia hybrida | Geranium dissectum | Montia perfoliata |
| Myosotis arvensis | Chenopodium album | Polygonum aviculare |
| Polygonum lapathifolium | Polygonum convolvulus | Galeopsis tetrahit |
| Chrysantemum segetum | Centaurea cyanus | Viola arvensis |
| Senecia vulgaris | Cirsium arvense | Fumaria officinalis |
| Raphanus raphanistrum | Agrostis stolonifera | Atriplex patula |
| Capsella bursa-pastoris | Thlaspi arvense | Portulaca oleracea |
| Setaria viridis | Eleusine indica | Euphorbia helioscopia |

The application rate of the compound of formula I in admixture with the a compound of group (2) and/or a compound of group (3) is usually in the range of 0.1 to 500 grams of active ingredient (g a.i.) per hectare, with rates between 2 to 100 g a.i./ha often achieving satisfactory control and selectivity. The optimal rate for a specific application will depend on the crop(s) under cultivation and the predominant species of infesting weed, and readily may be determined by established biological tests known to those skilled in the art.

The selection of the herbicidally active compound of group (2) as well as of the safening compound of group (3) will likewise be dependent on the crop/weed situation to be treated, and will be readily identifiable by those skilled in this area. The application rate of the herbicidally active compound of group (2) is usually in the range of 0.5 to 4000 grams, preferably 1.0 to 1000 grams of the active ingredient (g a.i.) per hectare. In another preferred embodiment preferred application rate of this active ingredient is in the range of 100 to 2500 g a.i./ha, preferably 100–1500 g a.i./ha.

The application rate of the safening compound of group (3) is usually in the range of 1 to 1500 grams, preferably 5 to 1250 grams of the active ingredient (g a.i.) per hectare.

The application rates the active components are determined primarily by the chemical type of the component, since the intrinsic activity of different types of herbicide/safeners vary widely.

For example the preferred application rate of a lipid biosynthesis inhibitors is in the range of 25 to 2500 g/ha, especially in the range of 25 to 400, preferably in the range of 25 to 250 g/ha; of a acetolactate synthase inhibitor in the range of 1 to 800 g/ha (for a sulfonyl urea type herbicide in the range of 7.5 to 100 g/ha); of a photosynthesis inhibitor in the range of 30 to 4000 g/ha (for an urea type herbicide in the range of 100 to 1500 g/ha; for a nitrile type herbicide in the range of 75 to 400 g/ha); of a protoporphyrinogen IX oxidase inhibitor in the range of 0.5 to 600 g/ha; of a bleacher herbicide in the range of 25 to 600 g/ha; of a EPSP-inhibitor in the range of 200 to 1200 g/ha; of a glutamine synthase inhibitor in the range of 10 to 600 g/ha; of a mitosis inhibitor in the range of 300 to 3000 g/ha (for a dinitroaniline type herbicide in the range of 250 to 2500 g/ha); of a cell division inhibitor in the range of 60 to 4000 g/ha; of a cellulose biosynthesis inhibitor in the range of 25 to 500 g/ha; of a auxin herbicide in the range of 25 to 2500 g/ha, especially in the range of 25 to 750 g/ha); of a auxin transport inhibitor in the range of 10 to 200 g/ha; of various other herbicides in the range of 10 to 2000 g/ha.

For example, the activity of a triazine herbicide, such as cyanazine or simazine, can be almost tenfold greater than that of an urea herbicide such as chlortoluron or isoproturon.

The optimal rate for the chosen component of group (2) will, however, depend on the crop(s) under cultivation and the level of weed infestation, and can readily be determined by established biological tests. Naturally, with such a wide variation in application rate for the component of group (b), the ratio of the compound of formula I to the component of group (2) in the present invention will be determinded predominantly by the choice of the component of group (b). The ratio (by weight) of the compound of formula I to the additional herbicidal compound of group (2) is as a rule, from 1:0.002 to 1:800, especially from 1:0.05 to 1:500, preferably from 1:0.1 to 1:200, in particular from 1:1 to 1:100. The preferred ratio formula I: group (2) may vary, as shown in the following table:

| Herbicide of group (2) | Preferred ratio formula I: group (2) | Most preferred ratio formula I: group (2) |
|---|---|---|
| Carfentrazone- | 1:0.05 to 1:20 | 1:0.1 to 1:10 |
| Cinidon-ethyl | 1:0.1 to 1:10 | 1:0.2 to 1:8 |
| Clodinafop | 1:0.05 to 1:20 | 1:0.2 to 1:10 |
| Fenoxaprop | 1:0.05 to 1:20 | 1:0.2 to 1:10 |
| Florasulam | 1:0.1 to 1:10 | 1:0.13 to 1:1 |
| Flufenacet | 1:0.5 to 1:50 | 1:1 to 1:25 |
| Flupyrsulfuron | 1:0.001 to 1:5 | 1:0.02 to 1:1 |
| Isoproturon | 1:0.5 to 1:150 | 1:1 to 1:100 |
| JV 485 | 1:0.5 to 1:50 | 1:1 to 1:20 |
| MCPA | 1:1 to 1:200 | 1:2 to 1:150 |
| Pendimethalin | 1:1 to 1:200 | 1:2 to 1:150 |
| Sulfosulfuron | 1:0.05 to 1:10 | 1:0.1 to 1:1 |

The application rates for the compounds of group (3) are determined primarily by the chemical type of the component. For example the preferred application rate for benoxacor is in the range of 50 to 250 g/ha; for cloquintocet in the range of 5 to 25 g/ha; for cyometrinil in the range of 25 to 500 g/ha; for dichlormid in the range of 150 to 500 g/ha; for dicyclon in the range of 150 to 250 g/ha; for dietholate in the range of 750 to 1250 g/ha; for fenchlorazole of 5 to 50 g/ha; for fenclorim in the range of 150 to 500 g/ha; for flurazole in the range of 100 to 500 g/ha; for fluoxefenim in the range of 100 to 500 g/ha; for furilazole in the range of 50 to 250 g/ha; for isoxadifen in the range of 25 to 250 g/ha; for mefenpyr in the range of 10 to 150 g/ha; for mephenate in the range o 10 to 1000 g/ha; for naphthalic anhydrid in the range of 250 to 1000 g/ha; for oxabetrinil in the range of 250 to 1000 g/ha and for R 29148 in the range of 50 to 250 g/ha.

The ratio (by weight) of the compound of formula I to the additional safening compound of group (3) is as a rule, from 1:0.002 to 1:800, especially from 1:0.05 to 1:100, preferably from 1:0.1 to 1:40, in particular from 1:1 to 1:20.

The active compounds can be used in the form of a mixture of separate formulations, typically mixed with water prior to application (tank-mixtures), or as separate formulations applied individually within a certain time interval. All the active compounds can also be formulated together in a suitable ratio according to the present invention, together with usual carriers and/or additives known in the art.

Accordingly, the invention further provides a herbicidal composition which comprises as active ingredient, a synergistically effective amount of at least one compound of formula I as defined above, and at least one compound selected from group (2) and/or the compound of selected from group (3) and one or more carriers. A method of making such a composition is also provided which comprises bringing the mixture of the compound of formula I and the compound selected from group (2) and/or the compound of group (3) as defined above into association with the carrier(s). It is also envisaged that different isomers or mixtures of isomers may have different levels or spectra of activity and thus compositions may comprise individual isomers or mixtures of isomers.

A composition according to the invention preferably contains from 0.5% to 95% by weight (w/w) of active ingredients.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including material which is normally a gas but which has been compressed to form a liquid.

The compositions may be manufactured into e.g. emulsion concentrates, solutions, oil in water emulsions, wettable powders, soluble powders, suspension concentrates, dusts, granules, water dispersible granules, micro-capsules, gels and other formulation types by well-established procedures. These procedures include intensive mixing and/or milling of the active ingredients with other substances, such as fillers, solvents, solid carriers, surface active compounds (surfactants), and optionally solid and/or liquid auxiliaries and/or adjuvants. The form of application such as spraying, atomizing, dispersing or pouring may be chosen like the compositions according to the desired objectives and the given circumstances.

Solvents (liquid carriers) may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different liquids are often suitable.

Solid carriers, which may be used for dusts, wettable powders, water dispersible granules, or granules, may be mineral fillers, such as calcite, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers may be calcite or sand. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to formula I and component of group (2) and/or component of group (3) to be formulated. Surfactants may also mean mixtures of individual surfactants.

The compositions of the invention may for example be formulated as wettable powders, water dispersible granules, dusts, granules, solutions, emulsifiable concentrates, emulsions, suspension concentrates and aerosols. Wettable powders usually contain 5 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient.

Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and retention enhancers (stickers), and water or an organic liquid in which the active ingredient is substantially insoluble; certain organic solids or inorganic salts may be present dissolved in the formulation to assist in preventing sedimentation and crystallization or as antifreeze agents for water.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the invention are:

| Emulsion Concentrate (EC) | | |
|---|---|---|
| Active Ingredient | Compound A + Isoproturon (1:16) | 30% (w/v) |
| Emulsifier(s) | Atlox ® 4856 B/Atlox ® 4858 B[1] (mixture containing calcium alkyl aryl sulfonate, fatty alcohol ethoxylates and light aromatics/mixture containing calcium alkyl aryl sulfonate, fatty alcohol ethoxylates and light aromatics) | 5% (w/v) |
| Solvent | Shellsol ® A[2] (mixture of $C_9$–$C_{10}$ aromatic hydrocarbons) | To 1000 ml |
| Suspension Concentrate (SC) | | |
| Active Ingredient | Compound A + Flufenacet (1:8) | 50% (w/v) |
| Dispersing agent | Soprophor ® FL[3] (polyoxyethylene polyaryl phenyl ether phosphate amine salt) | 3% (w/v) |
| Antifoaming agent | Rhodorsil ® 422[3] (nonionic aqueous emulsion of polydimethylsiloxanes) | 0.2% (w/v) |
| Structure agent | Kelzan ® S[4] (Xanthan gum) | 0.2% (w/v) |
| Antifreezing agent | Propylene glycol | 5% (w/v) |
| Biocidal agent | Proxel ®[5] (aqueous dipropylene glycol solution containing 20% 1,2-benisothiazolin-3-one) | 0.1% (w/v) |
| Water | | to 1000 ml |
| Wettable Powder (WP) | | |
| Active Ingredient | Compound A + MCPA (1:32) | 60% (w/w) |
| Wetting agent | Atlox ® 4995[1] (polyoxyethylene alkyl ether) | 2% (w/w) |
| Dispersing agent | Witcosperse ® D-60[6] (mixture of sodium salts of condensed naphthalene sulfonic acid and alkylarylpolyoxy acetates | 3% (w/w) |
| Carrier/ Filler | Kaolin | 35% (w/w) |
| Water Dispersible Granules (WG) | | |
| Active Ingredient | Compound A + Ioxynil (1:16) | 50% (w/w) |
| Dispersing/ Binding agent | Witcosperse ® D-450[6] (mixture of sodium salts of condensed naphthalene sulfonic acid and alkyl sulfonates) | 8% (w/w) |
| Wetting agent | Morwet ® EFW[6] (formaldehyde condensation product) | 2% (w/w) |
| Antifoaming agent | Rhodorsil ® EP 6703[3] (encapsulated silicone) | 1% (w/w) |
| Disintegrant | Agrimer ® ATF[7] (cross-linked homopolymer of N-vinyl-2-pyrrolidone) | 2% (w/w) |
| Carrier/ Filler | Kaolin | 35% (w/w) |

[1]commercially available from ICI Surfactants
[2]commercially available from Deutsche Shell AG
[3]commercially available from Rhône-Poulenc
[4]commercially available from Kelco Co.
[5]commercially available from Zeneca
[6]commercially available from Witco
[7]commercially available from International Speciality Products The compositions of this invention can also comprise other compounds having biological activity, e.g. compounds having similar or complementary pesticidal activity or compounds having plant growth regulating, fingicidal, bactericidal, nematicidal, algicidal, molluscicidal, rodenticidal or virusidal activity. It is also possible to include fertilizers, compounds which induce resistance into plants, biological control agents such as viruses, bacteria, nematodes, fungi and other microorganisms and/or repellents of birds and animals. These mixtures of pesticides can have a broader spectrum of activity than the synergistic composition according to this invention alone.

The following examples illustrate specific embodiments of the present invention; however, the invention is not limited to the embodiments so illustrated, but includes the entire scope of the appended claims.

EXAMPLES

General Method

The trials are carried out under greenhouse conditions in pre- and post-emergence applications. The plant seeds are sown in pots containing a loamy sand soil (0.5 l). The herbicides are applied as single treatments, or in a combination comprising a compound of formula I and compound selected from group (2) as defined above, before or after emergence of weeds and crop. The herbicidal performance is assessed as percent damage in comparison to the untreated control plants. The assessment is done 21 days after the treatment. Wheat and barley are treated at the 3–4 leaf stage, the broad-leaf weeds at the 2–4 leaf stage and annual grasses at the 2–3 leaf stage.

The following weeds have been included:

| Grass weeds: | ALOMY | *Alopecurus myosuroides* |
| | APESV | *Apera spica-venti* |
| | LOLPE | *Lolium perenne* |
| | SETVI | *Setaria viridis* |
| Broadleaf weeds: | GALAP | *Galium aparine* |
| | LAMPU | *Lamium purpureum* |
| | MATIN | *Matricaria inodora* |
| | PAPRH | *Papaver rhoeas* |
| | STEME | *Stellaria media* |
| | VERPE | *Veronica persica* |

For the compound of formula I Compound A is employed. The other component selected from group (2) is identified in each example by its common name with application rates (and hence component ratios) chosen to be appropriate to the established activity level of that component.

Flufenacet is the common name of N-(fluorophenyl)-N-(1-methylethyl)-2-[[5-(trifluoromethyl)-1,3,4-thiadiazol-2-yl]oxy]acetamide, which is disclosed for example in the German patent application DE 38 21 600.

Florasulam is the common name of N-(2,6-dichlorophenyl)-8-fluoro-5-methoxy-1,2,4-triazolo[1,5-c]pyrimidine-2-sulfonamide, which is disclosed for example in the U.S. Pat. No. 5,163,995.

Cinidon-ethyl is the common name of ethyl 2-chloro-3-[2-chloro-5-(1,3-dioxo-4,5,6,7-tetrahydroisoindol-2-yl)-phenyl-acrylate, which is disclosed for example by K. Grossmann, H. Schiffer, Pestic. Sci. (1999), 55(7), 687–695. CODEN: PSSCBG ISSN: 0031-613X.

JV 485 is the acronym for isopropyl 2-chloro-4-fluoro-5-(4-bromo-1-methyl-6-trifluoromethyl-pyrazol-3-yl)-benzoate of formula:

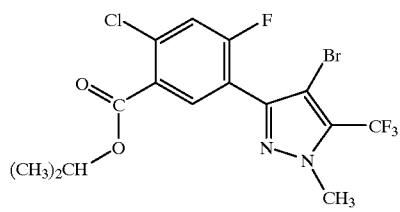

The following abbreviations have been used in the tables:

| WE: | expected response of a mixture by means of the Colby formula; |
| W: | observed response of a mixture. |

The results of these experiments are tabulated as Examples 1 to 14 wherein all the results from a chosen component of group (2) are collected under the same Example number, different dosage rates/test species being recorded in the examples. From these results, it is clear that synergism exists between the compounds of formula I and the compounds selected from group (2). Crop tolerance (wheat and barley) is excellent in all treatments.

Example 1A

Herbicidal Performance of the Mixture Compound A+Isoproturon (IPU) Against Grass and Broadleaf Weeds in Pre-Emergence Application

| Dose (g/ha) | Species | Compound A alone (% control) | IPU alone (% control) | WE | W |
|---|---|---|---|---|---|
| 3.75 + 60 | ALOMY | 0 | 43 | 43 | 68 |
| | LAMPU | 10 | 0 | 10 | 38 |
| | LOLPE | 5 | 40 | 43 | 60 |
| | PAPRH | 63 | 0 | 63 | 92 |
| | SETVI | 0 | 0 | 0 | 35 |
| | STEME | 0 | 15 | 15 | 83 |
| | VERPE | 13 | 0 | 13 | 35 |
| 3.75 + 120 | GALAP | 0 | 0 | 0 | 18 |
| | LAMPU | 10 | 15 | 24 | 65 |
| | SETVI | 0 | 20 | 20 | 68 |
| | VERPE | 13 | 0 | 13 | 38 |
| 3.75 + 240 | LAMPU | 10 | 70 | 73 | 88 |
| 7.5 + 60 | ALOMY | 5 | 43 | 46 | 65 |
| | SETVI | 35 | 0 | 35 | 53 |
| | STEME | 10 | 15 | 24 | 74 |
| | VERPE | 33 | 0 | 33 | 60 |
| 7.5 + 120 | SETVI | 35 | 20 | 48 | 73 |
| | VERPE | 33 | 0 | 33 | 88 |
| 7.5 + 240 | SETVI | 35 | 65 | 77 | 100 |
| | VERPE | 33 | 0 | 33 | 85 |
| 15 + 60 | STEME | 60 | 15 | 66 | 93 |

In all of the above treatments, the observed activity was clearly superior to the expected activity, thus demonstrating that the combination was synergistic.

Example 1B

Herbicidal Performance of the Mixture Compound A+Isoproturon (IPU) Against Grass and Broadleaf Weeds in Post-Emergence Application

| Dose (g/ha) | Species | Compound A alone (% control) | IPU alone (% control) | WE | W |
|---|---|---|---|---|---|
| 3.75 + 60 | ALOMY | 10 | 15 | 24 | 43 |
| | APESV | 25 | 50 | 63 | 93 |
| | LOLPE | 10 | 38 | 44 | 70 |
| | SETVI | 0 | 15 | 15 | 63 |
| | STEME | 10 | 25 | 33 | 95 |
| | VERPE | 80 | 15 | 83 | 99 |
| 3.75 + 120 | ALOMY | 10 | 38 | 44 | 77 |
| | SETVI | 0 | 40 | 40 | 73 |
| 3.75 + 240 | PAPRH | 30 | 48 | 64 | 99 |
| | VERPE | 80 | 5 | 81 | 98 |
| 7.5 + 60 | APESV | 35 | 50 | 68 | 97 |
| | LOLPE | 28 | 38 | 55 | 92 |
| | PAPRH | 65 | 0 | 65 | 80 |
| | SETVI | 23 | 15 | 35 | 68 |
| | STEME | 18 | 25 | 39 | 99 |
| 7.5 + 120 | ALOMY | 28 | 38 | 55 | 88 |
| | PAPRH | 65 | 25 | 74 | 98 |
| | SETVI | 23 | 40 | 54 | 92 |
| 7.5 + 240 | PAPRH | 65 | 48 | 82 | 99 |
| 15 + 60 | ALOMY | 45 | 15 | 53 | 84 |
| | APESV | 40 | 50 | 70 | 99 |
| | LAMPU | 83 | 0 | 83 | 99 |
| | LOLPE | 50 | 38 | 69 | 97 |
| | SETVI | 55 | 15 | 62 | 83 |
| | STEME | 45 | 25 | 59 | 98 |
| 15 + 120 | ALOMY | 45 | 38 | 66 | 90 |
| | SETVI | 55 | 40 | 73 | 96 |
| 30 + 60 | STEME | 70 | 25 | 78 | 100 |

In all of the above treatments, the observed activity was clearly superior to the expected activity, thus demonstrating that the combination was synergistic.

Example 2

Herbicidal Performance of the Mixture Compound A+Flufenacet Against Grass and Broadleaf Weeds in Pre-Emergence Application

| Dose (g/ha) | Species | Compound A alone (% control) | flufenacet alone (% control) | WE | W) |
|---|---|---|---|---|---|
| 3.75 + 15 | GALAP | 0 | 0 | 0 | 15 |
| | LOLPE | 15 | 30 | 41 | 75 |
| | MATIN | 50 | 0 | 50 | 65 |
| | PAPRH | 0 | 0 | 0 | 15 |
| | VERPE | 0 | 0 | 0 | 18 |
| 3.75 + 30 | MATIN | 50 | 0 | 50 | 80 |
| | PAPRH | 0 | 0 | 0 | 15 |
| | VERPE | 0 | 10 | 10 | 40 |
| 3.75 + 60 | PAPRH | 0 | 0 | 0 | 30 |
| | VERPE | 0 | 10 | 10 | 45 |
| 7.5 + 15 | PAPRH | 15 | 0 | 15 | 45 |
| | VERPE | 23 | 0 | 23 | 55 |
| 7.5 + 30 | GALAP | 0 | 10 | 10 | 40 |
| | PAPRH | 15 | 0 | 15 | 67 |
| | STEME | 5 | 0 | 5 | 25 |
| | VERPE | 23 | 10 | 31 | 73 |
| 7.5 + 60 | GALAP | 0 | 55 | 55 | 83 |
| | PAPRH | 15 | 0 | 15 | 70 |
| | VERPE | 23 | 10 | 31 | 99 |
| 15 + 15 | VERPE | 60 | 0 | 60 | 96 |
| 15 + 30 | GALAP | 10 | 10 | 19 | 43 |
| | VERPE | 60 | 10 | 64 | 95 |
| 15 + 60 | VERPE | 60 | 10 | 64 | 100 |

In all of the above treatments, the observed activity was clearly superior to the expected activity, thus demonstrating that the combination was synergistic.

Example 3

Herbicidal Performance of the Mixture Compound A+JV 485 Against Grass and Broadleaf Weeds in Pre-Emergence Application

| Dose (g/ha) | Species | Compound A alone (% control) | JV 485 alone (% control) | WE | W |
|---|---|---|---|---|---|
| 3.75 + 60 | ALOMY | 0 | 25 | 25 | 73 |
| 7.5 + 30 | ALOMY | 0 | 10 | 10 | 45 |
| 7.5 + 60 | ALOMY | 0 | 25 | 25 | 75 |
| 7.5 + 120 | ALOMY | 0 | 65 | 65 | 88 |
| 15 + 60 | GALAP | 0 | 0 | 0 | 20 |
| 30 + 60 | GALAP | 0 | 0 | 0 | 15 |
| 30 + 120 | GALAP | 0 | 63 | 63 | 92 |
| 60 + 60 | GALAP | 10 | 0 | 10 | 25 |

In all of the above treatments, the observed activity was clearly superior to the expected activity, thus demonstrating that the combination was synergistic.

Example 4

Herbicidal Performance of the Mixture Compound A+MCPA Against Grass and Broadleaf Weeds in Post-Emergence Application

| Dose (g/ha) | Species | Compound A alone (% control) | MCPA alone (% control) | WE | W |
|---|---|---|---|---|---|
| 3.75 + 120 | LAMPU | 20 | 0 | 20 | 50 |
| | SETVI | 15 | 25 | 36 | 80 |
| 3.75 + 240 | LAMPU | 20 | 0 | 20 | 50 |
| | SETVI | 15 | 43 | 52 | 73 |
| 3.75 + 480 | LAMPU | 20 | 13 | 30 | 55 |
| | STEME | 28 | 65 | 75 | 92 |
| 7.5 + 120 | LOLPE | 23 | 0 | 23 | 43 |
| 7.5 + 240 | ALOMY | 23 | 0 | 23 | 38 |
| | APESV | 50 | 0 | 50 | 73 |
| | LOLPE | 23 | 10 | 31 | 55 |
| 7.5 + 480 | ALOMY | 23 | 0 | 23 | 43 |
| 15 + 120 | ALOMY | 28 | 0 | 28 | 45 |
| 15 + 240 | ALOMY | 28 | 0 | 28 | 50 |
| 15 + 480 | ALOMY | 28 | 0 | 28 | 53 |
| 30 + 120 | ALOMY | 50 | 0 | 50 | 65 |
| 30 + 240 | ALOMY | 50 | 0 | 50 | 70 |
| 30 + 480 | ALOMY | 50 | 0 | 50 | 73 |

In all of the above treatments, the observed activity was clearly superior to the expected activity, thus demonstrating that the combination was synergistic.

Example 5

Herbicidal Performance of the Mixture Compound A+Flupyrsulfuron Against Grass and Broadleaf Weeds in Post-Emergence Application

| Dose (g/ha) | Species | Compound A alone (% control) | flupyrsulfuron alone (% control) | WE | W |
|---|---|---|---|---|---|
| 3.75 + 2.5 | SETVI | 0 | 0 | 0 | 23 |
| 3.75 + 5 | GALAP | 10 | 0 | 10 | 28 |
| 3.75 + 10 | GALAP | 10 | 0 | 10 | 28 |
|  | SETVI | 0 | 10 | 10 | 50 |
| 7.5 + 5 | GALAP | 23 | 0 | 23 | 40 |
|  | SETVI | 8 | 10 | 17 | 38 |
| 7.5 + 10 | ALOMY | 3 | 73 | 74 | 89 |
|  | SETVI | 8 | 10 | 17 | 60 |
| 15 + 5 | ALOMY | 8 | 53 | 57 | 80 |
| 15 + 10 | LOLPE | 23 | 10 | 31 | 55 |
|  | SETVI | 58 | 10 | 62 | 80 |
| 30 + 2.5 | APESV | 68 | 0 | 68 | 83 |
| 30 + 5 | ALOMY | 23 | 53 | 64 | 80 |
| 60 + 2.5 | ALOMY | 28 | 35 | 53 | 78 |
| 60 + 5 | ALOMY | 28 | 53 | 66 | 85 |

In all of the above treatments, the observed activity was clearly superior to the expected activity, thus demonstrating that the combination was synergistic.

Example 6

Herbicidal Performance of the Mixture Compound A+Sulfosulfuron Against Grass Weeds in Post-Emergence Application

| Dose (g/ha) | Species | Compound A alone (% control) | sulfosulfuron alone (% control) | WE | W |
|---|---|---|---|---|---|
| 30 + 3.75 | LOLPE | 60 | 18 | 67 | 83 |

In the above treatment, the observed activity was clearly superior to the expected activity, thus demonstrating that the combination was synergistic.

Example 7

Herbicidal Performance of the Mixture Compound A+Mecoprop Against Grass and Broadleaf Weeds in Post-Emergence Application

| Dose (g/ha) | Species | Compound A alone (% control) | mecoprop alone (% control) | WE | W |
|---|---|---|---|---|---|
| 3.75 + 240 | APESV | 10 | 0 | 10 | 38 |
|  | LAMPU | 20 | 10 | 28 | 53 |
| 3.75 + 480 | APESV | 10 | 0 | 10 | 43 |
| 3.75 + 960 | APESV | 10 | 0 | 10 | 58 |
| 7.5 + 240 | LAMPU | 35 | 10 | 42 | 70 |
| 15 + 240 | LAMPU | 50 | 10 | 55 | 83 |
| 15 + 480 | LAMPU | 50 | 48 | 74 | 93 |
| 30 + 960 | LOLPE | 65 | 0 | 65 | 88 |
| 60 + 240 | LOLPE | 75 | 0 | 75 | 92 |
| 60 + 480 | LOLPE | 75 | 0 | 75 | 94 |
| 60 + 960 | LOLPE | 75 | 0 | 75 | 91 |

In all of the above treatments, the observed activity was clearly superior to the expected activity, thus demonstrating that the combination was synergistic.

Example 8

Herbicidal Performance of the Mixture Compound A+Ioxynil Against Grass and Broadleaf Weeds in Post-Emergence Application

| Dose (g/ha) | Species | Compound A alone (% control) | ioxynil alone (% control) | WE | W |
|---|---|---|---|---|---|
| 3.75 + 60 | LAMPU | 20 | 0 | 20 | 63 |
| 3.75 + 120 | APESV | 10 | 0 | 10 | 25 |
|  | LAMPU | 20 | 15 | 32 | 73 |
| 3.75 + 240 | LAMPU | 20 | 28 | 42 | 90 |
| 7.5 + 60 | LAMPU | 35 | 0 | 35 | 90 |
| 7.5 + 120 | LAMPU | 35 | 15 | 45 | 89 |
| 7.5 + 240 | LAMPU | 35 | 28 | 53 | 96 |
| 15 + 60 | LAMPU | 50 | 0 | 50 | 97 |
| 15 + 120 | LAMPU | 50 | 15 | 58 | 98 |
| 15 + 240 | LAMPU | 50 | 28 | 64 | 100 |
| 60 + 240 | LOLPE | 75 | 0 | 75 | 90 |

In all of the above treatments, the observed activity was clearly superior to the expected activity, thus demonstrating that the combination was synergistic.

Example 9

Herbicidal Performance of the Mixture Compound A+Carfentrazone Against Grass and Broadleaf Weeds in Post-Emergence Application

| Dose (g/ha) | Species | Compound A alone (% control) | carfentrazone alone (% control) | WE | W |
|---|---|---|---|---|---|
| 3.75 + 15 | SETVI | 0 | 0 | 0 | 40 |
| 7.5 + 1.88 | SETVI | 5 | 0 | 5 | 23 |
| 7.5 + 15 | SETVI | 5 | 0 | 5 | 40 |
| 15 + 1.88 | MATIN | 48 | 0 | 48 | 63 |
|  | STEME | 70 | 0 | 70 | 90 |
| 15 + 15 | MATIN | 48 | 48 | 73 | 88 |

In all of the above treatments, the observed activity was clearly superior to the expected activity, thus demonstrating that the combination was synergistic.

Example 10

Herbicidal Performance of the Mixture Compound A+Cinidon-ethyl Against Grass and Broadleaf Weeds in Post-Emergence Application

| Dose (g/ha) | Species | Compound A alone (% control) | cinidon-ethyl alone (% control) | WE | W |
|---|---|---|---|---|---|
| 7.5 + 12.5 | MATIN | 13 | 53 | 59 | 78 |
| 7.5 + 25 | APESV | 20 | 0 | 20 | 35 |
|  | MATIN | 13 | 68 | 72 | 88 |
| 7.5 + 50 | SETVI | 15 | 0 | 15 | 35 |
| 3.75 + 25 | GALAP | 13 | 20 | 30 | 55 |
|  | MATIN | 5 | 68 | 70 | 93 |
|  | SETVI | 4 | 0 | 4 | 20 |
| 15 + 25 | GALAP | 20 | 20 | 36 | 60 |
|  | MATIN | 30 | 68 | 78 | 94 |
| 15 + 50 | APESV | 50 | 0 | 50 | 68 |
| 60 + 25 | GALAP | 55 | 20 | 64 | 80 |

In all of the above treatments, the observed activity was clearly superior to the expected activity, thus demonstrating that the combination was synergistic.

Example 11

Herbicidal Performance of the Mixture Compound A+Florasulam Against Grass Weeds in Post-Emergence Application

| Dose (g/ha) | Species | Compound A alone (% control) | florasulam alone (% control) | WE | W |
|---|---|---|---|---|---|
| 60 + 10 | LOLPE | 40 | 50 | 70 | 93 |

In the above treatment, the observed activity was clearly superior to the expected activity, thus demonstrating that the combination was synergistic.

Example 12

Herbicidal Performance of the Mixture Compound A+Clodinafop Against Grass and Broadleaf Weeds in Post-Emergence Application

| Dose (g/ha) | Species | Compound A alone (% control) | clodinafop alone (% control) | WE | W |
|---|---|---|---|---|---|
| 3.75 + 7.5 | ALOMY | 0 | 10 | 10 | 33 |
|  | LAMPU | 35 | 0 | 35 | 50 |
| 3.75 + 15 | APESV | 0 | 0 | 0 | 50 |
|  | LOLPE | 0 | 65 | 65 | 85 |
| 3.75 + 30 | APESV | 0 | 15 | 15 | 58 |
| 7.5 + 7.5 | LAMPU | 55 | 0 | 55 | 75 |
| 7.5 + 15 | LAMPU | 55 | 0 | 55 | 75 |
| 15 + 7.5 | ALOMY | 0 | 10 | 10 | 28 |
|  | GALAP | 0 | 0 | 0 | 20 |
| 15 + 15 | GALAP | 0 | 0 | 0 | 20 |
| 15 + 30 | GALAP | 0 | 0 | 0 | 55 |
| 30 + 7.5 | ALOMY | 10 | 10 | 19 | 35 |
|  | GALAP | 20 | 0 | 20 | 100 |
| 30 + 15 | APESV | 53 | 0 | 53 | 70 |
|  | GALAP | 20 | 0 | 20 | 45 |
| 30 + 30 | GALAP | 20 | 0 | 20 | 75 |

In all of the above treatments, the observed activity was clearly superior to the expected activity, thus demonstrating that the combination was synergistic.

Example 13

Herbicidal Performance of the Mixture Compound A+Fenoxaprop Against Grass and Broadleaf Weeds in Post-Emergence Application

| Dose (g/ha) | Species | Compound A alone (% control) | fenoxaprop alone (% control) | WE | W |
|---|---|---|---|---|---|
| 3.75 + 30 | ALOMY | 3 | 0 | 3 | 43 |
| 7.5 + 30 | ALOMY | 5 | 0 | 5 | 30 |
|  | APESV | 10 | 58 | 62 | 80 |
|  | MATIN | 15 | 0 | 15 | 30 |
|  | STEME | 30 | 0 | 30 | 68 |
| 7.5 + 60 | STEME | 30 | 0 | 30 | 60 |
| 15 + 30 | ALOMY | 8 | 0 | 8 | 33 |
| 30 + 15 | LOLPE | 28 | 3 | 30 | 60 |
| 30 + 30 | ALOMY | 15 | 0 | 15 | 38 |
| 30 + 60 | LOLPE | 28 | 43 | 59 | 79 |
| 60 + 15 | ALOMY | 43 | 0 | 43 | 58 |
| 60 + 30 | ALOMY | 43 | 0 | 43 | 58 |
| 60 + 60 | LOLPE | 63 | 43 | 79 | 94 |

In all of the above treatments, the observed activity was clearly superior to the expected activity, thus demonstrating that the combination was synergistic.

Example 14

Herbicidal Performance of the Mixture Compound A+Pendimethalin Against Grass and Broadleaf Weeds in Post-Emergence Application

| Dose (g/ha) | Species | Compound A alone (% control) | pendimethalin alone (% control) | WE | W |
|---|---|---|---|---|---|
| 3.75 + 120 | GALAP | 40 | 23 | 54 | 70 |
| 3.75 + 480 | SETVI | 0 | 40 | 40 | 65 |
| 7.5 + 120 | APESV | 5 | 5 | 10 | 28 |
| 7.5 + 240 | APESV | 5 | 40 | 43 | 58 |
| 15 + 120 | APESV | 10 | 5 | 15 | 30 |
| 30 + 240 | ALOMY | 15 | 15 | 28 | 55 |
| 60 + 120 | ALOMY | 33 | 0 | 33 | 58 |
| 60 + 240 | ALOMY | 33 | 15 | 43 | 65 |

In all of the above treatments, the observed activity was clearly superior to the expected activity, thus demonstrating that the combination was synergistic.

What is claimed is:

1. A herbicidal composition comprising a combination of constituents (1) and (2), a combination of constituents (1) and (3), or a combination of constituents (1), (2) and (3), wherein (1) is at least one 2-phenyl-4-(hetero-)aryloxypyrimidine of formula I:

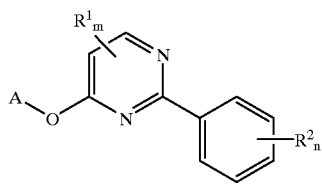

(I)

wherein
A represents an optionally substituted phenyl group or an optionally substituted 5- or 6-membered nitrogen-containing heteroaromatic group or a difluorobenzodioxolyl group;
m represents an integer from 0 to 2;
n represents an integer from 0 to 5;
$R^1$ (or each $R^1$) independently represents a halogen atom, an optionally substituted alkyl, alkenyl, alkynyl, alkoxy, alkoxyalkyl, dialkoxyalkyl, alkoxyalkoxy, alkylthio, amino, alkylamino, dialkylamino, alkoxyamino or formamido group;
$R^2$ (or each $R^2$) independently represents a halogen atom, an optionally substituted alkyl, alkenyl, alkynyl, haloalkyl, haloalkoxy, alkoxy, alkoxyalkyl, alkoxyalkoxy, alkylthio, haloalkylthio group or a nitro, cyano, $SF_5$ or a alkylsulfonyl or alkylsulfinyl group;
or an environmentally compatible salt thereof;
(2) is at least one additional herbicidal compound, which is active against broadleaved weeds and/or annual grasses; and
(3) is at least one additional safening compound, wherein the constituents are combined in synergistically herbicidally effective amounts.

2. A herbicidal composition according to claim 1 comprising a 2-phenyl-4-(hetero-)aryloxypyrimidine of formula I, wherein
A represents a phenyl group being substituted by one chlorine or fluorine atom, or one methyl, trifluoromethyl, trifluoromethoxy or difluoromethoxy group;
m is 0; and
n is 1 or 2.

3. A herbicidal composition according to claim 2 wherein the 2-phenyl-4-(hetero-)aryloxypyrimidine of formula I is 4-(3-trifluoromethylphenoxy)-2-(4-trifluoromethylphenyl)-pyrimidine.

4. A herbicidal composition according to claim 1, wherein (2) is selected from
a) lipid biosynthesis inhibitors;
b) acetolactate synthase inhibitors (ALS);
c) photosynthesis inhibitors;
d) protoporphyrinogen-IX-oxidase inhibitors;
e) bleacher herbicides;
f) enolpyruvylshikimate 3-phosphate synthase inhibitors (EPSP);
g) glutamine synthetase inhibitors;
h) dihydropteroate synthase inhibitors (DHP);
i) mitosis inhibitors;
j) cell division inhibitors;
k) cellulose biosynthesis inhibitors;
l) uncoupling herbicides;
m) auxin herbicides;
n) auxin transport inhibitors; and
o) various other herbicides.

5. A herbicidal composition according to claim 1, wherein (2) is selected from
a) a lipid biosynthesis inhibitor: chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, propaquizafop, quizalofop, quizalofop-P, trifop, alloxydim, butroxydim, clethodim, cloproxydim, cycloxydim, profoxydim, sethoxydim, tepraloxydim, tralkoxydim, butylate, cycloate, di-allate, dimepiperate, EPTC, esprocarb, ethiolate, isopolinate, methiobencarb, molinate, orbencarb, pebulate, prosulfocarb, sulfallate, thiobencarb, tiocarbazil, tri-allate, vernolate, bensulide, benfuserate and ethofumesate;
b) an acetolactate synthase inhibitor:
a sulfonyl urea type herbicide: amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, tnifloxysulfuron, triflusulfuron, tritosulfuron, propoxycarbazon and flucarbazon;
a sulfonamide type herbicide: chloransulam, diclosulam, florasulam, flumetsulam, metosulam and penoxsulam;
an imidazolinone type herbicide: imazamethbenz, imazamox, imazapic, imazapyr, imazaquin and imazethapyr;
a pyrimidyl ether: bispyribac, pynibenzoxim, pyniftalid, pyrithiobac and pyriminobac;
c) a photosynthesis inhibitor:
a photosynthetic electron transport inhibitor:
a tniazine type herbicide: ametryn, atraton, atrazine, aziprotryne, chlorazine, cyanatryn, cyanazine, cyprazine, desmetryne, dimethamethryn, dipropetryn, egliazine, ipazine, mesoprazine, methometon, methoprotryn, procyazine, proglinazine, prometon, prometryn, propazine, sebuthylazine, secbumeton, simazine, simeton, simetryn, terbumeton, terbutylazine, terbutryn and trietazine;
a urea type herbicide: anisuron, benzthiazuron, buthiuron, buturon, chlorbromuron, chloreturon, chlorotoluron, chloroxuron, difenoxuron, dimefuron, diuron, ethidimuron, fenuron, flometuron, fluothiuron, isoproturon, isouron, linuron, methabenzthiazuron, methiuron, metobenzuron, metobromuron, metoxuron, monoisouron, monolinuron, monuron, neburon, parafluron, phenobenzuron, siduron, tebuthiuron, tetrafluron, thiadiazuron and thiazafluron;
another photosynthesis inhibitor:
a nitrile type herbicide: bromobonil, bromoxynil, chloroxynil, iodobonil and ioxynil;
a triazinone type herbicide: ametridione, amibuzin, hexazinone, isomethiozin, metamitron and metribuzin;

a urazil type herbicide: bromacil, isocil, lenacil and terbacil;
a pyridazinone type herbicide: brompyrazon, chioridazon and dimidazon;
a phenylcarbamate type herbicide: desmedipham, phenisopham and phenmedipham;
an amide type herbicide: propanil;
a benzothiadiazole type herbicide: bentazone;
a phenyl paridazine type herbicide: pyridate and pyridafol;
a bipyridylium type herbicide: cyperquat, diethamquat, difenzoquat, diquat, morfamquat and paraquat;
amicarbazone, bromofenoxim, flumezin, methazole and pentanochior;
d) a protoporphyrinogen IX oxidase inhibitor:
a diphenyl ether type herbicide: acifluorfen, bifenox, chiomethoxyfen, chiornitrof en, ethoxyfen, fluorodifen, fluoroglycofen, fluoronitrofen, fomesafen, furyloxyf en, halosafen, lactofen, nitrofen, nitrofluorfen and oxyfluorfen;
an N-phenylphthalimide type herbicide: cinidon-ethyl, flumiclorac, flumioxazin and flumipropyn;
a thiadiazole type herbicide: fluthiacet and thidiazimin;
an oxadiazole type herbicide: oxadiazon and oxadiargyl;
azafenidin, carfentrazone, sulfentrazone, pentoxazone, benzfendizone, butafenacil, pyraclonil, profluazol, flufenpyr, flupropacil, nipyraclofen, etnipromid, fluazolate (JV 485) and pyraflufen;
e) a bleacher herbicide: metfiurazon, norfiurazon, diflufenican, flufenican, picolinaf en, beflubutamid, fluridone, flurochloridone, flurtamone, isoxachlortole, isoxaflutole, mesotrione, sulcotrione, benzofenap, parazolynate, pyrazoxyfen, benzobicyclon, amitrol, clomazone, aclonifen, ketospiradox and a 3-heterocyclyl substituted benzoyl derivative of formula:

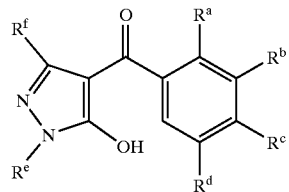

in which the variables have the following meanings:
$R^a$, $R^c$ are hydrogen, halogen, $C_{1-6}$-alkyl, $C_{1-6}$-haloalkyl, $C_{1-6}$-alkoxy, $C_{1-6}$-haloalkoxy, $C_{1-6}$-alkylthio, $C_{1-6}$-alkylsulfinyl or $C_{1-6}$-alkylsulfonyl;
$R^b$ is a heterocyclic radical selected from the group:
thiazol-2-yl, thiazol-4-yl, thiazol-5-yl, isoxazol-3-yl, isoxazol-4-yl, isoxazol-5-yl, 4,5-dihydroisoxazol-3-yl, 4,5-dihydroisoxazol-4-yl and 4,5-dihydroisoxazol-5-yl, it being possible for the nine radicals mentioned to be unsubstituted or mono- or polysubstituted by halogen, $C_{1-4}$-alkyl, $C_{1-4}$-alkoxy, $C_{1-4}$-haloalkyl, $C_{1-4}$-haloalkoxy or $C_{1-4}$-alkylthio;
$R^d$ is hydrogen, halogen or $C_{1-6}$-alkyl;
$R^e$ is $C_{1-6}$-alkyl;
$R^f$ is hydrogen or $C_{1-6}$-alkyl;
f) an enolpyruvylshikimate 3-phosphate synthase inhibitor (EPSP): glyphosate;
g) a glutamine synthetase inhibitor: bilanaphos and glufosinate;

h) a dihydropteroate synthase inhibitor (DHP): asulam;
i) a mitosis inhibitor:
a dinitroaniline type herbicide: benfluralin, butralin, dinitramin, athalfluralin, fluchloralin, isopropalin, methapropalin, nitralin, oryzalin, pendimethalin, prodiamine, profluralin and trifluralin;
a phosphoramidate type herbicide: amiprofos-methyl and butamifos;
a pyridazine type herbicide: dithiopyr and thiazopyr;
propyzamid, tebutam, chlorthal, carbetamide, chlorbufam, chlorpropham and propham;
j) a cell division inhibitor:
a chloracetamide type herbicide: acetochlor, alachlor, allidochlor, butachlor, butenachlor, CDEA, delachlor, diethatyl, dimethachlor, dimethenamid, dimethenamid-P, epronaz, metazachior, metolachior, S-metolachlor, pethoxamid, pretilachior, propachior, propisochlor, prynachior, terbuchior, thenyichior and xylachlor;
an acetamide type herbicide: diphenamid, napropamide and naproanilide;
an oxacetamide type herbicide: flufenacet and mefenacet;
fentrazamide, anilophos, piperophos, cafenstrole, indanof an and tridiphane;
k) a cellulose biosynthesis inhibitor: dichlobenil, chiorthiamid, isoxaben and fluproxam;
l) an uncoupling herbicide: dinofenate, dinoprop, dinosam, dinoseb, dinoterb, DNOC, etinof en and medinoterb;
m) an auxin herbicide: clomeprop, 2,4-D, 2,4-DB, dichiorprop, dichlorprop-P, MCPA, MCPA thioethyl, MCPB, mecoprop, mecoprop-P, 2,4,5-T, chloramben, dicamba, 2,3,6-TBA, tricamba, quinchlorac, quinmerac, clopyralid, fluroxypyr, picloram, N trichlopyr and benazolin;
n) an auxin transport inhibitor: naptalame and diflufenzopyr;
o) various other herbicides:
a flurene carboxylic acid: chlorflurenol and flurenol;
benzoylprop, flamprop, flamprop-M, bromobutide, cinmethylin, cumyluron, daimuron, methyldymron, etobenzanid, fosamm, metam, pyributicarb, oxaziclomefone, dazomet, triaziflam and methylbromid;

and environmentally compatible salts, esters, thioesters and amides thereof.

6. A herbicidal composition according to claim 1, wherein (2) is selected from
a) a lipid biosynthesis inhibitor;
b) an acetolactate synthase inhibitor;
c) a photosynthesis inhibitor;
d) a protoprophyrinogen IX oxidase inhibitor;
i) a mitosis inhibitor;
j) a cell division inhibitor;
m) an auxine herbicide; and
o) a flurene carboxylic acid herbicide.

7. A herbicidal composition according to claim 6, wherein (2) is selected from
b) a sulfonyl urea type herbicide and a sulfonamide type herbicide;
c) a urea-type herbicide, a triazine type herbicide, a nitrile type herbicide or a phenyl pyrazine type herbicide;

i) a dinitroaniline type herbicide, j) an oxyacetamide herbicide.

8. A herbicidal composition according to claim 6, wherein (2) is selected from
- a) fenoxaprop and clodinafop;
- b) amidosulfuron, flupyrsulfuron, sulfosulfuron, florasulam and metosulam;
- c) atrazine, cyanazine, simazine, chlorotoluron, isoproturon, linuron, neburon, bromoxynil, ioxynil and pyridate;
- d) cinidon-ethyl, carfentrazone and JV 485;
- i) pendimethalin;
- j) flufenacet;
- m) dichlorprop, MCPA, mecoprop and fluroxypyr; and
- o) flurenol.

9. A herbicidal composition according to claim 1, wherein (3) is selected from benoxacor, cloquintocet, cyometrinil, dichlorimid, dicyclon, dietholate, fenchlorazole, fenclorim, flurazole, fluxofenim, furilazole, isoxdifen, mefenpyr, mephenate, naphthalic anhydride, oxabenil and R 29148.

10. A herbicidal composition according to claim 9, wherein (3) is selected from benoxacor, cloquintocet, dichlormid, fenchlorazole, fenclorim, fluxofenim, furilazole, isoxdifen, mefenpyr and oxabenil.

11. A herbicidal composition according to claim 1, comprising the combination of (1) and (2).

12. A herbicidal composition according to claim 1, comprising the combination of (1) and (3).

13. A herbicidal composition according to claim 1, comprising the combination of (1), (2) and (3).

14. A herbicidal composition according to claim 1, wherein (1) and (2) are combined in a ratio (by weight) of from 1:0.002 to 1:800.

15. A herbicidal composition as claimed in claim 14, wherein the ratio (by weight) of (1) to (2) is from 1:0.05 to 1:500.

16. A herbicidal composition as claimed in claim 15, wherein the ratio (by weight) of (1) to (2) is from 1:1 to 1:100.

17. A herbicidal composition as claimed in claim 1, wherein (1) and (3) are combined in a ratio (by weight) of from 1:0.002 to 1:800.

18. A herbicidal mixture comprising a herbicidally ffective amount of the herbicidal composition defined in claim 1 and one or more carriers.

19. A method of controlling the growth of weeds at a locus which comprises applying to the locus an effective amount of the herbicidal composition defined in claim 1 before, during and/or after the emergence of undesired plants, it being possible for the active components to be applied simultaneously or in succession.

20. A method according to claim 19, wherein the constituents of the combination are applied together in a single formulation.

21. A method according to claim 19, wherein the constituents of the combination are applied in separate formulations.

22. A method for controlling the growth of weeds in cereal crops which comprises applying thereto an effective amount of the composition defined in claim 1.

23. A method of combating *Alopecurus myosuroides, Apera spica-venti, Lolium perenne, Setaria viridis, Galium aparine, Lamium purpureum, Matricaria inodora, Papaver rhoeas, Stellana media* and/or *Veronica persica* at a locus which comprises applying to the locus a herbicidally effective amount of the composition defined in claim 1.

* * * * *

UNITED STATES PATENT AND TRADEMARK OFFICE
CERTIFICATE OF CORRECTION

PATENT NO. : 6,683,027 B2
DATED : January 27, 2004
INVENTOR(S) : Baltruschat et al.

It is certified that error appears in the above-identified patent and that said Letters Patent is hereby corrected as shown below:

Column 32,
Line 22, "chiorimuron" should be -- chlorimuron --;
Line 31, "tnifloxysulfuron" should be -- trifloxysulfuron --;
Line 33, "chioransulam" should be -- chloransulam --;
Line 39, "pynibenzoxim" should be -- pyribenzoxim --;
Line 40, "pyniftalid" should be -- pyriftalid --;
Line 43, "tniazine" should be -- triazine --.

Column 33,
Line 17, "chiomethoxyfen, chiornitrof en" should be -- chlomethoxyfen, chlornitrofen --;
Line 30, "metfiurazon, norfiurazon" should be -- metflurazon, norflurazon --;
Line 31, "picolinaf en" should be -- picolinafen --.

Column 34,
Line 17, "metazachior, metolachior" should be -- metazachlor, metolachlor --;
Line 18, "pretilachior, propachior" should be -- pretilachlor, propachlor --;
Line 19, "prynachior, terbuchior, thenylichior" should be -- prynachlor, terbuchlor, thenyichlor --;
Line 28, "chiorthiamid" should be -- chlorthiamid --;
Line 30, "etinof en" should be -- etinofen --;
Line 33, "dichiorprop" should be -- dichlorprop --;
Line 37, "N trichlo-" should be -- trichlo- --;
Line 45, "fosamm" should be -- fosamin --

UNITED STATES PATENT AND TRADEMARK OFFICE
CERTIFICATE OF CORRECTION

PATENT NO. : 6,683,027 B2
DATED : January 27, 2004
INVENTOR(S) : Baltruschat et al.

It is certified that error appears in the above-identified patent and that said Letters Patent is hereby corrected as shown below:

Column 35,
Line 26, "isoxdif en" should be -- isoxdifen --.

Signed and Sealed this

Twenty-ninth Day of June, 2004

JON W. DUDAS
*Acting Director of the United States Patent and Trademark Office*